United States Patent [19]

Krause et al.

[11] Patent Number: 4,715,984
[45] Date of Patent: Dec. 29, 1987

[54] LIQUID-CRYSTALLINE DIHYDROAZINES

[75] Inventors: Joachim Krause, Dieburg; Wächtler, Griesheim; Bernhard Scheuble, Alsbach, all of Fed. Rep. of Germany

[73] Assignee: Merck Patent Gesellschaft mit beschrankter Haftung, Darmstadt, Fed. Rep. of Germany

[21] Appl. No.: 821,195

[22] Filed: Jan. 22, 1986

[30] Foreign Application Priority Data

Jan. 22, 1985 [DE] Fed. Rep. of Germany ....... 3501849

[51] Int. Cl.⁴ .................... C09K 19/34; G02F 1/13; C07D 265/06; C07D 279/06; C07D 319/06; C07D 339/08; C07D 413/12; C07D 417/12
[52] U.S. Cl. .................... 252/299.61; 252/299.5; 350/350 R; 350/350 S; 534/567; 544/53; 544/54; 544/55; 544/72; 544/88; 544/96; 544/97
[58] Field of Search .................... 252/299.5, 299.61; 350/350 R, 350 S; 534/567; 544/53, 54, 55, 72, 96, 97, 88

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,200,580 | 4/1980 | Hsu | 252/299.61 |
| 4,322,354 | 3/1982 | Sorkin | 252/299.61 |
| 4,325,830 | 4/1982 | Sethofer | 252/299.61 |
| 4,335,011 | 6/1982 | Sethofer | 252/299.61 |
| 4,344,856 | 8/1982 | Demus et al. | 252/299.61 |
| 4,356,104 | 10/1982 | Hsu | 252/299.61 |
| 4,358,393 | 11/1982 | Zaschke et al. | 252/299.61 |
| 4,389,329 | 6/1983 | Boller et al. | 252/299.5 |
| 4,450,094 | 5/1989 | Sato et al. | 252/299.61 |
| 4,462,923 | 7/1984 | Boller et al. | 252/299.61 |
| 4,510,069 | 4/1985 | Eidenschink et al. | 252/299.61 |
| 4,521,327 | 6/1985 | Demus et al. | 252/299.61 |
| 4,565,425 | 1/1986 | Petrzilka et al. | 252/299.61 |
| 4,609,485 | 9/1986 | Kitand et al. | 252/299.61 |

FOREIGN PATENT DOCUMENTS

| | | | |
|---|---|---|---|
| 87679 | 9/1983 | European Pat. Off. | 252/299.61 |
| 104011 | 3/1984 | European Pat. Off. | 252/299.61 |
| 152697 | 8/1985 | European Pat. Off. | 252/299.61 |
| 2257588 | 6/1973 | Fed. Rep. of Germany | 252/299.61 |
| 3315295 | 10/1984 | Fed. Rep. of Germany | 252/299.61 |
| 3404116 | 8/1985 | Fed. Rep. of Germany | 252/299.61 |
| 3405914 | 8/1985 | Fed. Rep. of Germany | 252/299.61 |
| 3411571 | 10/1985 | Fed. Rep. of Germany | 252/299.61 |
| 144423 | 10/1980 | German Democratic Rep. | 252/299.61 |
| 158480 | 1/1983 | German Democratic Rep. | 252/299.61 |
| 60-25973 | 2/1985 | Japan | 252/299.61 |
| 60-109569 | 6/1985 | Japan | 252/299.61 |
| 60-149564 | 8/1985 | Japan | 252/299.61 |
| 61-24571 | 2/1986 | Japan | 252/299.61 |
| 2092169 | 8/1982 | United Kingdom | 252/299.61 |
| 2161808 | 1/1986 | United Kingdom | 252/299.61 |

OTHER PUBLICATIONS

Bolotim, B. M. et al., Advances in Liquid Crystal Res. & Appls., Bata, L., Ed., Pergamon Press, Oxford, pp. 1015–1018 (1980).

Demus, D., et al., Flüssige Kristalle in Tabellen II, Veb Deutscher Verlag fur Grumdstoffindustrie, Leipzig, pp. 343–400 (1984).

Pavluchenko, A. I., et al., Advances in Liquid Crystal Research & Applications., Bata, L., Ed., Pergamon Press, Oxford, pp. 1007–1012 (1980).

Grachev, V. T., et al., Mol. Cryst. Liq. Cryst., vol. 65, pp. 133–144 (1981).

Pavluchenko, A. I., et al., J. De Physique, Coll C3, Suppl. No. 4, vol. 40, pp. C3-1–C3-4(1979).

Karamysheva, L. A., et al. Mol. Cryst. Liq. Cryst., vol. 67, pp. 241–252 (1981).

Pavluchenko, A. I., et al., Mol. Cryst. Liq. Cryst., vol. 37, pp. 35–46 (1976).

Zaschke, H., Advances in Liquid Crystal Research & Application, Ed. Bata, L., Pergamon Press, Oxford, pp. 1059–1074 (1980).

Primary Examiner—Teddy S. Gron
Attorney, Agent, or Firm—Millen & White

[57] ABSTRACT

Dihydroazines of the formula I

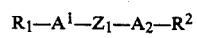

$$R_1-A^1-Z_1-A_2-R^2 \qquad I$$

wherein $R^1$, $R^2$, $A^1$, $A^2$ and $Z_1$ have the meanings specified herein may be used as components of liquid crystalline phases.

18 Claims, No Drawings

LIQUID-CRYSTALLINE DIHYDROAZINES

SUMMARY OF THE INVENTION

It is an object of this invention to provide new stable liquid crystalline or mesogenic compounds which are suitable as components of liquid crystalline phases.

Upon further study of the specification and appended claims, further objects and advantages of this invention will become apparent to those skilled in the art.

These objects have been achieved by providing 5,6-dihydroazines of the formula I

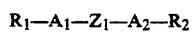

wherein $R^1$ and $R^2$ denote alkyl having 1-5 C atoms in which one or two nonadjacent $CH_2$ groups may also be replaced by —O—, —CO—, —O—CO—, —CO—O— and/or —CH=CH—, one of the radicals $R^1$ and $R^2$ also denotes H, F, Cl, Br, CN, $R^3$—$A^3$—$Z^2$, denotes —A—, —$A^4$—A—, —A—$A^4$—, denotes

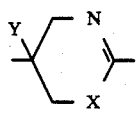

in which X may be O or S and Y may be H, $C_1$–$C_4$-alkyl, F, Cl, Br, CN, $A^2$, $A^3$ and $A^4$ denote in each case a 1,4-cyclohexylene, 1,3-dioxane-2,5-diyl of a 1,3-dithiane-2,5-diyl group which in each case may be substituted in the 1- or 4-, 2- or 5- and 2- or 5-position, respectively, by $C_1$–$C_4$-alkyl, F, Cl, Br, $CF_3$, or CN, a piperidine-1,4-diyl or 1,4-bicyclo[2.2.2]-octylene group, A or an unsubstituted 1,4-phenylene group or a 1,4-phenylene group substituted by one or two F and/or Cl atoms and/or $CH_3$ groups and/or CN groups, and/or in which one or two CH groups may also be replaced by N, $Z^1$ and $Z^2$ denote in each case —CO—O—, —O—CO—, —$CH_2CH_2$—, —CHCN—$CH_2$—, —$CH_2$—CHCN—, —CH=CH—, —$OCH_2$—, —$CH_2O$—, —CH=N—, —N=CH—, —NO=N—, —N=NO— or a single bond and denotes alkyl having 1-15 C atoms, in which one or two nonadjacent $CH_2$ groups may be replaced by —O—, —CO—, —O—CO—, —CO—O— and/or —CH=CH—, or denotes H, F, Cl, Br or CN, and also the acid addition salts of the basic compounds among these compounds.

For the sake of simplicity in what follows Cy denotes a 1,4-cyclohexylene group, Oaz a 5,6-dihydro-1,3(4H)-oxazine-2,5-diyl group, Taz a 5,6-dihydro-1,3(4H)-thiazine-2,5-diyl group, Dio a 1,3-dioxane-2,5-diyl group, Dit a 1,3-dithiane-2,5-diyl group, Bi a bicyclo[2.2.2]octylene group, Pip a piperidine-1,4-diyl group, Phe a 1,4-phenylene group, Pyr a pyrimidine-2,5-diyl group and Pyn a pyridazine-3,6-diyl group, it being possible for Phe and/or Pyr and/or Pyn to be unsubstituted or substituted by one or two F and/or Cl atoms and/or $CH_3$ groups and/or CN groups.

The compounds of the formula I can be used as components of liquid-crystalline phases in particular for displays which are based on the principle of the twisted cell, the guest-host effect, the effect of deformation of aligned phases or the dynamic scattering effect.

It was found that the compounds of the formula I are excellently suitable as components of liquid crystalline phases. In particular stable liquid crystalline phases with wide mesophase ranges and comparatively low viscosity can be prepared using them.

Moreover, the compounds of the formula I are remarkable for particularly advantageous values of the ratio of the elastic constants.

In addition, the provision of the compounds of the formula I quite generally extends substantially the range of liquid crystalline substances which are suitable for the preparation of liquid crystalline mixtures from various applicational points of view.

The compounds of the formula I have a wide field of application. Depending on the choice of the substituents these compounds may be used as basic materials of which liquid crystalline phases are predominantly composed; however, compounds of the formula I may also be added to liquid crystalline basic materials from other classes of compound in order, for example, to influence the dielectric and/or optical anisotropy of such a dielectric. The compounds of the formula I are furthermore suitable as intermediate products for the manufacture of other substances which may be used as components of liquid crystalline dielectrics.

DETAILED DISCUSSION

The compounds of the formula I are in the pure state colorless and form liquid crystalline mesophases in a temperature range beneficially disposed for electrooptical application. They are very stable chemically, thermally and towards light.

The subject of the invention is therefore the compounds of the formula I and also a process for the preparation of compounds of the formula I wherein a compound which otherwise corresponds to the formula I but contains instead of H atoms one or more reducible groups and/or C—C bonds is treated with a reducing agent, or that a carboxylic acid or thiocarboxylic acid amide is cyclized with a 2-substituted 1,3-dihalopropane or a 2-substituted 3-halopropylamine, or that a 2-substituted N-acyl-3-hydroxypropylamine is cyclized with a base or phosphorous pentasulphide or a 2-substituted N-acyl-3-mercaptopropylamine is cyclized, or that to prepare compounds of the formula I, in which $R^1$ and/or $R^2$ and/or $R^3$ denote F, Cl, Br or CN, the diazonium group in a corresponding diazonium salt is replaced by F, Cl, Br or CN, or that to prepare esters of the formula I (in which $Z^1$ and/or $Z^2$ denote —CO—O— or —O—CO— and/or $R^1$ and/or $R^2$ and/or $R^3$ contain a carboxyl group) a corresponding carboxylic acid or one of its reactive derivatives is reacted with a corresponding alcohol or one of its reactive derivatives, or that to prepare nitriles of the formula I (in which $R^1$ and/or $R^2$ and/or $R^3$ denote CN and/or in which $A^2$ and/or $A^3$ and/or $A^4$ is substituted by at least one CN group) a corresponding carboxylic acid amide is dehydrated or a corresponding carboxylic acid halide is reacted with sulfamide, or that to prepare ethers of the formula I (in which $R^1$ and/or $R^2$ and/or $R^3$ denote an alkoxy group and/or $Z^1$ and/or $Z^2$ is a —OCH$_2$— or —CH$_2$O— group) a corresponding hydroxy compound is etherified, and/or that optionally a chloro or bromo compound of the formula I (in which $R^1$ and/or $R^2$ and/or $R^3$ denote Cl or Br and/or in which $A^2$ and/or $A^3$ and/or $A^4$ is substituted by at least one chlorine or bromine atom) is reacted with a cyanide, and/or that optionally a base of the formula I is converted into one of its acid addition salts by treatment with an acid, of that optionally a compound of the formula I is liberated from one of its acid addition salts by treatment with a base.

Moreover, an object of the invention is the use of the compounds of the formula I as components of liquid crystalline phases. An object of the invention is furthermore liquid crystalline phases with a content of at least one compound having the structural element 5,6-dihydro-1,3(4H)-oxazine-2,5-diyl or 5,6-dihydro-1,3(4H)-thiazine-2,5-diyl, in particular a compound of the formula I, as well as liquid crystalline display elements which contain such phases. Phases of this type have particularly advantageous elastic constants.

Above and below $R^1$, $R^2$, $R^3$, $A^1$, $A^2$, $A^3$, $A^4$, A, $Z^1$ and $Z^2$ have the specified meaning provided something else is not expressly indicated.

The compounds of the formula I comprise accordingly compounds with two rings of the partial formulae Ia and Ib:

$R^1$—A—$Z^1$—$A^2$—$R^2$   Ia $R^1$—A—$A^2$—$R^2$   Ib

Compounds with three rings of the partial formulae Ic to Il:

$R^1$—$A^4$—A—$Z^1$—$A^2$—$R^2$   Ic $R^1$—A—$A^4$—$Z^1$—$A^2$—$R^2$   Id $R^1$—A—$Z^1$—$A^2$—$Z^2$—$A^3$—$R^3$   Ie $R^3$—$A^3$—$Z^2$—A—$Z^1$—$A^2$—$R^2$   If $R^1$—A—$Z^1$—$A^2$—$A^3$—$R^2$   Ig $R^1$—A—$A^2$—$Z^2$—$A^3$—$R^3$   Ih $R^3$—$A^3$—$Z^2$—A—$A^2$—$R^2$   Ii $R^3$—$A^3$—A—$Z^1$—$A^2$—$R^2$   Ij $R^1$—$A^4$—A—$A^2$—$R^2$   Ik $R^1$—A—$A^4$—$A^2$—$R^2$   Il,

Compounds with four rings of the partial formulae Im to Iff:

$R^3$—$A^3$—$Z^2$—A—$Z^1$—$A^2$—$Z^2$—$A^3$—$R^3$   Im $R^3$—$A^3$—A—$Z^1$—$A^2$—$A^3$—$R^3$   In $R^3$—$A^3$—$Z^2$—A—$A^2$—$A^3$—$R^3$   Io $R^3$—$A^3$—A—$A^2$—$Z^2$—$A^3$—$R^3$   Ip $R^1$—$A^4$—A—$Z^1$—$A^2$—$Z^2$—$A^3$—$R^3$   Iq $R^3$—$A^3$—$Z^2$—$A^4$—A—$Z^1$—$A^2$—$R^2$   Ir $R^1$—A—$A^4$—$Z^1$—$A^2$—$Z^2$—$A^3$—$R^3$   Is $R^3$—$A^3$—$Z^2$—A—$A^4$—$Z^1$—$A^2$—$R^2$   It $R^1$—$A^4$—A—$A^2$—$A^3$—$R^3$   Iu $R^1$—A—$A^4$—$A^2$—$A^3$—$R^3$   Iv $R^1$—$A^4$—A—$A^2$—$Z^2$—$A^3$—$R^3$   Iw $R^1$—A—$A^4$—$A^2$—$Z^2$—$A^3$—$R^3$   Ix $R^1$—$A^4$—A—$Z^1$—$A^2$—$A^3$—$R^3$   Iy $R^1$—A—$A^4$—$Z^1$—$A^2$—$A^3$—$R^3$   Iz $R^3$—$A^3$—$A^4$—A—$A^2$—$R^2$   Iaa $R^3$—$A^3$—A—$A^4$—$A^2$—$R^2$   Ibb $R^3$—$A^3$—$A^4$—A—$Z^1$—$A^2$—$R^2$   Icc $R^3$—$A^3$—A—$A^4$—$Z^1$—$A^2$—$R^2$   Idd $R^3$—$A^3$—$Z^2$—$A^4$—A—$A^2$—$R^2$   Iee $R^3$—$A^3$—$Z^2$—A—$A^4$—$A^2$—$R^2$,   Iff and also compounds with five rings of the partial formulae Igg to Ill:

$R^3$—$A^3$—$Z^2$—$A^4$—A—$Z^1$—$A^2$—$Z^2$—$A^3$—$R^3$   Igg $R^3$—$A^3$—$Z^2$—A—$A^4$—$Z^1$—$A^2$—$Z^2$—$A^3$—$R^3$   Ihh $R^3$—$A^3$—$A^4$—A—$A^2$—$A^3$—$R^3$   Iii $R^3$—$A^3$—A—$A^4$—$A^2$—$A^3$—$R^3$   Ijj $R^3$—$A^3$—$A^4$—A—$Z^1$—$A^2$—$A^3$—$R^3$   Ikk $R^3$—$A^3$—A—$A^4$—$Z^1$—$A^2$—$A^3$—$R^3$.   Ill

In the compounds of the formulae above and below $R^1$, $R^2$ and $R^3$ preferably denote alkyl and in addition alkoxy.

Moreover, compounds of the formulae above and below are preferred in which one of the radicals $R^1$, $R^2$ and $R^3$ denotes CN, F or Cl.

$A^2$, $A^3$ and $A^4$ are preferably Cy, Phe, Dio or Pyr and also preferred are Oaz or Taz; preferably the compound of the formula I contains no more than one of the radicals Oaz, Taz, Dio, Dit, Pip, Bi, Pyn or Pyr in a particular case.

$Z^1$ and $Z^2$ are preferably single bonds, —CO—O—, —O—CO— or —CH$_2$CH$_2$— groups being secondarily preferred.

$R^3$ is preferably an alkyl group with 1-10 C atoms or CN.

If $R^1$ and/or $R^2$ denote alkyl radicals and/or alkoxy radicals, then they may be straight-chain or branched. Preferably they are straight-chain, have 2, 3, 4, 5, 6 or 7 C atoms and consequently preferably denote ethyl, propyl, butyl, pentyl, hexyl, heptyl, ethoxy, propoxy, butoxy, pentoxy, hexoxy or heptoxy, and also methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Compounds of the formulae I with branched end groups $R^1$ or $R^2$ or $R^3$ may occasionally be of significance because of better solubility in the usual liquid crystalline basic materials, in particular however as chiral dopants if they are optically active.

Branched groups of this type as a rule contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

Formula I comprises both the racemates of these compounds and also the optical antipodes as well as mixtures thereof.

Among the compounds of the formulae I and also Ia to III those compounds are preferred in which at least one of the radicals contained therein has one of the specified preferred meanings. Particularly preferred smaller groups of compounds are those of the formulae I1 to I38:

$R^1$-Oaz-COO-Phe-$R^2$   I1

$R^1$-Oaz-CH$_2$CH$_2$-Phe-$R^2$   I2

$R^1$-Oaz-Phe-COO-Phe-$R^2$   I3

$R^1$-Oaz-Phe-CH$_2$CH$_2$-Phe-$R^2$   I4

$R^1$-Oaz-Phe-CH$_2$CH$_2$-Cy-$R^2$   I5

$R^1$-Oaz-Phe-CH$_2$CH$_2$-Phe-Cy-$R^3$   I6

$R^1$-Oaz-Phe-CH$_2$CH$_2$-Phe-Dio-$R^3$   I7

$R^1$-Oaz-Phe-$R^2$   I8

$R^1$-Oaz-Phe-Phe-$R^2$   I9

$R^1$-Oaz-Phe-Phe-Cy-$R^3$   I10

$R^1$-Oaz-Phe-Phe-Dio-$R^3$   I11

$R^1$-Oaz-Cy-Phe-$R^2$   I12

$R^1$-Cy-Oaz-Phe-$R^2$   I13

$R^1$-Oaz-Cy-$R^3$   I14

$R^1$-Oaz-Cy-Cy-$R^3$   I15

$R^1$-Oaz-Pyr-$R^2$   I16

$R^1$-Oaz-CH$_2$CH$_2$-Phe-Phe-$R^2$   I17

$R^1$-Oaz-CH$_2$CH$_2$-Phe-Phe-Cy-$R^3$   I18

$R^1$-Oaz-CH$_2$CH$_2$-Phe-Phe-Cy-$R^2$   I19

$R^1$-Taz-COO-Phe-$R^2$   I20

$R^1$-Taz-CH$_2$CH$_2$-Phe-$R^2$   I21

$R^1$-Taz-Phe-COO-Phe-$R^2$   I22

$R^1$-Taz-Phe-CH$_2$CH$_2$-Phe-$R^2$   I23

$R^1$-Taz-Phe-CH$_2$CH$_2$-Cy-$R^2$   I24

$R^1$-Taz-Phe-CH$_2$CH$_2$-Phe-Cy-$R^3$   I25

$R^1$-Taz-CH$_2$CH$_2$-Phe-Dio-$R^3$   I26

$R^1$-Taz-Phe-$R^2$   I27

$R^1$-Taz-Phe-Phe-$R^2$   I28

$R^1$-Taz-Phe-Phe-Cy-$R^3$   I29

$R^1$-Taz-Phe-Phe-Dio-$R^3$   I30

$R^1$-Taz-Cy-Phe-$R^2$   I31

$R^1$-Cy-Taz-Phe-$R^2$   I32

$R^1$-Taz-Pyr-$R^2$   I33

$R^1$-Taz-CH$_2$CH$_2$-Phe-Phe-$R^2$   I34

$R^1$-Taz-CH$_2$CH$_2$-Phe-Phe-Cy-$R^2$   I35

$R^1$-Taz-CH$_2$CH$_2$-Phe-Cy-$R^2$   I36

$R^1$-Taz-Cy-$R^3$   I37

$R^1$-Taz-Cy-Cy-$R^3$   I38

In the compounds of the formula I those stereoisomers are preferred in which the Cy, Dio, Dit and/or Pip rings are trans-1,4-disubstituted. Those of the above-named formulae which contain one or more Oaz, Taz, Dio, Dit, Pip and/or Pyr groups encompass in each case the two possible 2,5-(Oaz, Taz, Dio, Dit, Pyr) or 1,4-positional isomers (Pip).

In the compounds of the formula I in which $A^1$ denotes an Oaz or Taz ring substituted by $R^1$ in the 2-position, $R^1$ preferably denotes alkyl.

Particularly preferred are compounds of the formula I in which $R^1$ and $R^2$ denote straight-chain or at most singly branched alkyl groups or alkoxy groups having 1-10 C atoms or CN in each particular case.

Particularly preferred are the following smaller groups of compounds in which -A- denotes 5,6-dihydro-1,3(4H)-thiazine-2,5-diyl or 5,6-dihydro-1,3(4H)-oxazine-2,5-diyl, Phe denotes 1,4-phenylene, Cyc denotes 1,4-cyclohexylene, Dio denotes 1,3-dioxane-2,5-diyl and Pyr denotes pyrimidine-2,5-diyl.

Alkyl preferably denotes straight-chain methyl, ethyl, propyl, butyl, pentyl, hexyl, heptyl, octyl, nonyl or decyl; oxaalkyl preferably denotes straight-chain 2-oxypropyl (=methoxymethyl), 2-(=ethoxymethyl)

or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 6-, 7- or 8-oxanonyl, 2-, 3-, 4-, 5-, 6-, 7-, 8- or 9-oxadecyl. Certain groups of compounds of this invention include:

(I)

Alkyl-A-Phe-CN
Alkyl-A-Phe-Methyl
Alkyl-A-Phe-Ethyl
Alkyl-A-Phe-Propyl
Alkyl-A-Phe-Butyl
Alkyl-A-Phe-Pentyl
Alkyl-A-Phe-Hexyl
Alkyl-A-Phe-Heptyl
Alkyl-A-Phe-Octyl
Alkyl-A-Phe-Nonyl
Alkyl-A-Phe-Decyl (II)

Alkyl-A-Phe-Methoxy
Alkyl-A-Phe-Ethoxy
Alkyl-A-Phe-Propoxy
Alkyl-A-Phe-Butoxy
Alkyl-A-Phe-Pentoxy
Alkyl-A-Phe-Hexoxy
Alkyl-A-Phe-Heptoxy
Alkyl-A-Phe-Octoxy
Alkyl-A-Phe-Nonoxy
Alkyl-A-Phe-Decoxy
Alkyl-A-(3-F-Phe)-CN (III)

Alkyl-A-Cyn-CN
Alkyl-A-Cyc-Methyl
Alkyl-A-Cyc-Ethyl
Alkyl-A-Cyc-Propyl
Alkyl-A-Cyc-Butyl
Alkyl-A-Cyc-Pentyl
Alkyl-A-Cyc-Hexyl
Alkyl-A-Cyc-Heptyl
Alkyl-A-Cyc-Octyl
Alkyl-A-Cyc-Nonyl
Alkyl-A-Cyc-Decyl (IV)

Alkyl-A-Cyc-Methoxy
Alkyl-A-Cyc-Ethoxy
Alkyl-A-Cyc-Propoxy
Alkyl-A-Cyc-Butoxy
Alkyl-A-Cyc-Pentoxy
Alkyl-A-Cyc-Hexoxy
Alkyl-A-Cyc-Heptoxy
Alkyl-A-Cyc-Octoxy
Alkyl-A-Cyc-Nonoxy
Alkyl-A-Cyc-Decoxy (V)

Alkyl-A-Cyc-Methoxycarbonyl
Alkyl-A-Cyc-Ethoxycarbonyl
Alkyl-A-Cyc-Propoxycarbonyl
Alkyl-A-Cyc-Butoxycarbonyl
Alkyl-A-Cyc-Pentoxycarbonyl
Alkyl-A-Cyc-Hexoxycarbonyl
Alkyl-A-Cyc-Heptoxycarbonyl
Alkyl-A-Cyc-Octoxycarbonyl
Alkyl-A-Cyc-Nonoxycarbonyl
Alkyl-A-Cyc-Decoxycarbonyl (VI)

Alkyl-A-Cyc-Methylcarbonyloxy
Alkyl-A-Cyc-Ethylcarbonyloxy
Alkyl-A-Cyc-Propylcarbonyloxy
Alkyl-A-Cyc-Butylcarbonyloxy
Alkyl-A-Cyc-Pentylcarbonyloxy
Alkyl-A-Cyc-Hexylcarbonyloxy
Alkyl-A-Cyc-Heptylcarbonyloxy
Alkyl-A-Cyc-Octylcarbonyloxy
Alkyl-A-Cyc-Nonylcarbonyloxy
Alkyl-A-Cyc-Decylcarbonyloxy (VII)

Methyl-A-Cyc-Oxaalkyl
Ethyl-A-Cyc-Oxaalkyl
Propyl-A-Cyc-Oxaalkyl
Butyl-A-Cyc-Oxaalkyl
Pentyl-A-Cyc-Oxaalkyl
Hexyl-A-Cyc-Oxaalkyl
Heptyl-A-Cyc-Oxaalkyl
Octyl-A-Cyc-Oxaalkyl
Nonyl-A-Cyc-Oxaalkyl
Decyl-A-Cyc-Oxaalkyl (VIII)

Alkyl-A-Phe-CN
Alkyl-A-Phe-Phe-Methyl
Alkyl-A-Phe-Phe-Ethyl
Alkyl-A-Phe-Phe-Propyl
Alkyl-A-Phe-Phe-Butyl
Alkyl-A-Phe-Phe-Pentyl
Alkyl-A-Phe-Phe-Hexyl
Alkyl-A-Phe-Phe-Heptyl
Alkyl-A-Phe-Phe-Octyl
Alkyl-A-Phe-Phe-Nonyl
Alkyl-A-Phe-Phe-Decyl
Alkyl-A-Phe-(3-F-Phe)-CN (IX)

Alkyl-A-Phe-Phe-Methoxy
Alkyl-A-Phe-Phe-Ethoxy
Alkyl-A-Phe-Phe-Propoxy
Alkyl-A-Phe-Phe-Butoxy
Alkyl-A-Phe-Phe-Pentoxy
Alkyl-A-Phe-Phe-Hexoxy
Alkyl-A-Phe-Phe-Heptoxy
Alkyl-A-Phe-Phe-Octoxy
Alkyl-A-Phe-Phe-Nonoxy
Alkyl-A-Phe-Phe-Decoxy (X)

Alkyl-A-Cyc-Phe-CN
Alkyl-A-Cyc-Phe-Methyl
Alkyl-A-Cyc-Phe-Ethyl
Alkyl-A-Cyc-Phe-Propyl
Alkyl-A-Cyc-Phe-Butyl
Alkyl-A-Cyc-Phe-Pentyl
Alkyl-A-Cyc-Phe-Hexyl
Alkyl-A-Cyc-Phe-Heptyl
Alkyl-A-Cyc-Phe-Octyl
Alkyl-A-Cyc-Phe-Nonyl
Alkyl-A-Cyc-Phe-Decyl
Alkyl-A-Cyc-(3-F-Phe)-CN (XI)

Alkyl-A-Cyc-Phe-Methoxy

Alkyl-A-Cyc-Phe-Ethoxy
Alkyl-A-Cyc-Phe-Propoxy
Alkyl-A-Cyc-Phe-Butoxy
Alkyl-A-Cyc-Phe-Pentoxy
Alkyl-A-Cyc-Phe-Hexoxy
Alkyl-A-Cyc-Phe-Heptoxy
Alkyl-A-Cyc-Phe-Octoxy
Alkyl-A-Cyc-Phe-Nonoxy
Alkyl-A-Cyc-Phe-Decoxy (XII)

Alkyl-A-Cyc-Cyc-CN
Alkyl-A-Cyc-Cyc-Methyl
Alkyl-A-Cyc-Cyc-Ethyl
Alkyl-A-Cyc-Cyc-Propyl
Alkyl-A-Cyc-Cyc-Butyl
Alkyl-A-Cyc-Cyc-Pentyl
Alkyl-A-Cyc-Cyc-Hexyl
Alkyl-A-Cyc-Cyc-Heptyl
Alkyl-A-Cyc-Cyc-Octyl
Alkyl-A-Cyc-Cyc-Nonyl
Alkyl-A-Cyc-Cyc-Decyl (XIII)

Alkyl-Cyc-A-Phe-CN
Alkyl-Cyc-A-Phe-Methyl
Alkyl-Cyc-A-Phe-Ethyl
Alkyl-Cyc-A-Phe-Propyl
Alkyl-Cyc-A-Phe-Butyl
Alkyl-Cyc-A-Phe-Pentyl
Alkyl-Cyc-A-Phe-Hexyl
Alkyl-cyc-A-Phe-Heptyl
Alkyl-Cyc-A-Phe-Octyl
Alkyl-Cyc-A-Phe-Nonyl
Alkyl-Cyc-A-Phe-Decyl
Alkyl-Cyc-A-(3-F-Phe)-CN (XIV)

Alkyl-Cyc-A-Phe-Methoxy
Alkyl-Cyc-A-Phe-Ethoxy
Alkyl-Cyc-A-Phe-Propoxy
Alkyl-Cyc-A-Phe-Butoxy
Alkyl-Cyc-A-Phe-Pentoxy
Alkyl-Cyc-A-Phe-Hexoxy
Alkyl-Cyc-A-Phe-Heptoxy
Alkyl-Cyc-A-Phe-Octoxy
Alkyl-Cyc-A-Phe-Nonoxy
Alkyl-Cyc-A-Phe-Decoxy (XV)

Cyan-Cyc-Phe-Phe-A-Alkyl
Methyl-Cyc-Phe-Phe-A-Alkyl
Ethyl-Cyc-Phe-Phe-A-Alkyl
Propyl-Cyc-Phe-Phe-A-Alkyl
Butyl-Cyc-Phe-Phe-A-Alkyl
Pentyl-Cyc-Phe-Phe-A-Alkyl
Hexyl-Cyc-Phe-Phe-A-Alkyl
Heptyl-Cyc-Phe-Phe-A-Alkyl
Octyl-Cyc-Phe-Phe-A-Alkyl
Nonyl-Cyc-Phe-Phe-A-Alkyl
Decyl-Cyc-Phe-Phe-A-Alkyl (XVI)

Alkyl-A-Pyr-Methyl
Alkyl-A-Pyr-Ethyl
Alkyl-A-Pyr-Propyl
Alkyl-A-Pyr-Butyl
Alkyl-A-Pyr-Pentyl
Alkyl-A-Pyr-Hexyl
Alkyl-A-Pyr-Heptyl
Alkyl-A-Pyr-Octyl
Alkyl-A-Pyr-Nonyl
Alkyl-A-Pyr-Decyl (XVII)

Alkyl-A-Pyr-Phe-CN (XVIII)

Alkyl-A-COO-Phe-CN
Alkyl-A-COO-Phe-Methyl
Alkyl-A-COO-Phe-Ethyl
Alkyl-A-COO-Phe-Propyl
Alkyl-A-COO-Phe-Butyl
Alkyl-A-COO-Phe-Pentyl
Alkyl-A-COO-Phe-Hexyl
Alkyl-A-COO-Phe-Heptyl
Alkyl-A-COO-Phe-Octyl
Alkyl-A-COO-Phe-Nonyl
Alkyl-A-COO-Phe-Decyl (XIX)

Alkyl-A-COO-Phe-Methoxy
Alkyl-A-COO-Phe-Ethoxy
Alkyl-A-COO-Phe-Propoxy
Alkyl-A-COO-Phe-Butoxy
Alkyl-A-COO-Phe-Pentoxy
Alkyl-A-COO-Phe-Hexoxy
Alkyl-A-COO-Phe-Heptoxy
Alkyl-A-COO-Phe-Octoxy
Alkyl-A-COO-Phe-Nonoxy
Alkyl-A-COO-Phe-Decoxy (XX)

Alkyl-A-COO-Cyc-CN
Alkyl-A-COO-Cyc-Methyl
Alkyl-A-COO-Cyc-Ethyl
Alkyl-A-COO-Cyc-Propyl
Alkyl-A-COO-Cyc-Butyl
Alkyl-A-COO-Cyc-Pentyl
Alkyl-A-COO-Cyc-Hexyl
Alkyl-A-cOO-Cyc-Heptyl
Alkyl-A-COO-Cyc-Octyl
Alkyl-A-COO-Cyc-Nonyl
Alkyl-A-COO-Cyc-Decyl (XXI)

Alkyl-A-COO-Phe-Phe-CN
Alkyl-A-COO-Phe-Phe-Methyl
Alkyl-A-COO-Phe-Phe-Ethyl
Alkyl-A-COO-Phe-Phe-Propyl
Alkyl-A-COO-Phe-Phe-Butyl
Alkyl-A-COO-Phe-Phe-Pentyl
Alkyl-A-COO-Phe-Phe-Hexyl
Alkyl-A-COO-Phe-Phe-Heptyl
Alkyl-A-COO-Phe-Phe-Octyl
Alkyl-A-COO-Phe-Phe-Nonyl
Alkyl-A-COO-Phe-Phe-Decyl (XXII)

Alkyl-A-Phe-COO-Cyc-CN
Alkyl-A-Phe-COO-Cyc-Methyl
Alkyl-A-Phe-COO-Cyc-Ethyl
Alkyl-A-Phe-COO-Cyc-Propyl
Alkyl-A-Phe-COO-Cyc-Butyl
Alkyl-A-Phe-COO-Cyc-Pentyl
Alkyl-A-Phe-COO-Cyc-Hexyl Alkyl-A-Phe-COO-Cyc-Heptyl
Alkyl-A-Phe-COO-Cyc-Octyl
Alkyl-A-Phe-COO-Cyc-Nonyl
Alkyl-A-Phe-COO-Cyc-Decyl (XXIII)

Alkyl-A-Phe-COO-Phe-CN
Alkyl-A-Phe-COO-Phe-Methyl
Alkyl-A-Phe-COO-Phe-Ethyl
Alkyl-A-Phe-COO-Phe-Propyl
Alkyl-A-Phe-COO-Phe-Butyl
Alkyl-A-Phe-COO-Phe-Pentyl
Alkyl-A-Phe-COO-Phe-Hexyl
Alkyl-A-Phe-COO-Phe-Heptyl
Alkyl-A-Phe-COO-Phe-Octyl
Alkyl-A-Phe-COO-Phe-Nonyl
Alkyl-A-Phe-COO-Phe-Decyl (XXIV)

Alkyl-A-Phe-COO-Phe-Methoxy
Alkyl-A-Phe-COO-Phe-Ethoxy
Alkyl-A-Phe-COO-Phe-Propoxy
Alkyl-A-Phe-COO-Phe-Butoxy
Alkyl-A-Phe-COO-Phe-Pentoxy
Alkyl-A-Phe-COO-Phe-Hexoxy
Alkyl-A-Phe-COO-Phe-Heptoxy
Alkyl-A-Phe-COO-Phe-Octoxy
Alkyl-A-Phe-COO-Phe-Nonoxy
Alkyl-A-Phe-COO-Phe-Decoxy (XXV)

Alkyl-A-Phe-COO-(3-F-Phe)-CN
Alkyl-A-Phe-CH$_2$CH$_2$-(3-F-Phe)-CN
Alkyl-A-Phe-CH$_2$O-(3-F-Phe)-CN (XXVI)

Alkyl-A-Cyc-COO-Cyc-CN
Alkyl-A-Cyc-COO-Cyc-Methyl
Alkyl-A-Cyc-COO-Cyc-Ethyl
Alkyl-A-Cyc-COO-Cyc-Propyl
Alkyl-A-Cyc-COO-Cyc-Butyl
Alkyl-A-Cyc-COO-Cyc-Pentyl
Alkyl-A-Cyc-COO-Cyc-Hexyl
Alkyl-A-Cyc-COO-Cyc-Heptyl
Alkyl-A-Cyc-COO-Cyc-Octyl
Alkyl-A-Cyc-COO-Cyc-Nonyl
Alkyl-A-Cyc-COO-Cyc-Decyl (XXVII)

Alkyl-A-Cyc-COO-Phe-CN
Alkyl-A-Cyc-COO-Phe-Methyl
Alkyl-A-Cyc-COO-Phe-Ethyl
Alkyl-A-Cyc-COO-Phe-Propyl
Alkyl-A-Cyc-COO-Phe-Butyl
Alkyl-A-Cyc-COO-Phe-Pentyl
Alkyl-A-Cyc-COO-Phe-Hexyl
Alkyl-A-Cyc-COO-Phe-Heptyl
Alkyl-A-Cyc-COO-Phe-Octyl
Alkyl-A-Cyc-COO-Phe-Nonyl
Alkyl-A-Cyc-COO-Phe-Decyl (XXVIII)

Alkyl-A-Cyc-COO-Phe-Methoxy
Alkyl-A-Cyc-COO-Phe-Ethoxy
Alkyl-A-Cyc-COO-Phe-Propoxy
Alkyl-A-Cyc-COO-Phe-Butoxy
Alkyl-A-Cyc-COO-Phe-Pentoxy
Alkyl-A-Cyc-COO-Phe-Hexoxy
Alkyl-A-Cyc-COO-Phe-Heptoxy
Alkyl-A-Cyc-COO-Phe-Octoxy
Alkyl-A-Cyc-COO-Phe-Nonoxy
Alkyl-A-Cyc-COO-Phe-Decoxy (XXIX)

Alkyl-A-OCO-Cyc-Methyl
Alkyl-A-OCO-Cyc-Ethyl
Alkyl-A-OCO-Cyc-Propyl
Alkyl-A-OCO-Cyc-Butyl
Alkyl-A-OCO-Cyc-Pentyl
Alkyl-A-OCO-Cyc-Hexyl
Alkyl-A-OCO-Cyc-Heptyl
Alkyl-A-OCO-Cyc-Octyl
Alkyl-A-OCO-Cyc-Nonyl
Alkyl-A-OCO-Cyc-Decyl (XXX)

Alkyl-A-OCO-Phe-Methyl
Alkyl-A-OCO-Phe-Ethyl
Alkyl-A-OCO-Phe-Propyl
Alkyl-A-OCO-Phe-Butyl
Alkyl-A-OCO-Phe-Pentyl
Alkyl-A-OCO-Phe-Hexyl
Alkyl-A-OCO-Phe-Heptyl
Alkyl-A-OCO-Phe-Octyl
Alkyl-A-OCO-Phe-Nonyl
Alkyl-A-OCO-Phe-Decyl (XXXI)

Alkyl-A-OCO-Phe-Methoxy
Alkyl-A-OCO-Phe-Ethoxy
Alkyl-A-OCO-Phe-Propoxy
Alkyl-A-OCO-Phe-Butoxy
Alkyl-A-OCO-Phe-Pentoxy
Alkyl-A-OCO-Phe-Hexoxy
Alkyl-A-OCO-Phe-Heptoxy
Alkyl-A-OCO-Phe-Octoxy
Alkyl-A-OCO-Phe-Nonoxy
Alkyl-A-OCO-Phe-Decoxy (XXXII)

Alkyl-A-OCO-Dio-Methyl
Alkyl-A-OCO-Dio-Ethyl
Alkyl-A-OCO-Dio-Propyl
Alkyl-A-OCO-Dio-Butyl
Alkyl-A-OCO-Dio-Pentyl
Alkyl-A-OCO-Dio-Hexyl
Alkyl-A-OCO-Dio-Heptyl
Alkyl-A-OCO-Dio-Octyl
Alkyl-A-OCO-Dio-Nonyl
Alkyl-A-OCO-Dio-Decyl (XXXIII)

Alkyl-A-CH$_2$CH$_2$-Phe-Phe-CN
Alkyl-A-CH$_2$CH$_2$-Phe-Phe-Methyl
Alkyl-A-CH$_2$CH$_2$-Phe-Phe-Ethyl
Alkyl-A-CH$_2$CH$_2$-Phe-Phe-Propyl
Alkyl-A-CH$_2$CH$_2$-Phe-Phe-Butyl
Alkyl-A-CH$_2$CH$_2$-Phe-Phe-Pentyl
Alkyl-A-CH$_2$CH$_2$-Phe-Phe-Hexyl
Alkyl-A-CH$_2$CH$_2$-Phe-Phe-Heptyl
Alkyl-A-CH$_2$CH$_2$-Phe-Phe-Octyl
Alkyl-A-CH$_2$CH$_2$-Phe-Phe-Nonyl
Alkyl-A-CH$_2$CH$_2$-Phe-Phe-Decyl (XXXIV)

Alkyl-A-CH$_2$CH$_2$-Phe-(2-F-Phe)-CN

Alkyl-A-CH₂CH₂-Phe-(2-F-Phe)-Methyl
Alkyl-A-CH₂CH₂-Phe-(2-F-Phe)-Ethyl
Alkyl-A-CH₂CH₂-Phe-(2-F-Phe)-Propyl
Alkyl-A-CH₂CH₂-Phe-(2-F-Phe)-Butyl
Alkyl-A-CH₂CH₂-Phe-(2-F-Phe)-Pentyl
Alkyl-A-CH₂CH₂-Phe-(2-F-Phe)-Hexyl
Alkyl-A-CH₂CH₂-Phe-(2-F-Phe)-Heptyl
Alkyl-A-CH₂CH₂-Phe-(2-F-Phe)-Octyl
Alkyl-A-CH₂CH₂-Phe-(2-F-Phe)-Nonyl
Alkyl-A-CH₂CH₂-Phe-(2-F-Phe)-Decyl (XXXV)

Alkyl-A-CH₂CH₂-Phe-(2-F-Phe)-Methoxy
Alkyl-A-CH₂CH₂-Phe-(2-F-Phe)-Ethoxy
Alkyl-A-CH₂CH₂-Phe-(2-F-Phe)-Propoxy
Alkyl-A-CH₂CH₂-Phe-(2-F-Phe)-Butoxy
Alkyl-A-CH₂CH₂-Phe-(2-F-Phe)-Pentoxy
Alkyl-A-CH₂CH₂-Phe-(2-F-Phe)-Hexoxy
Alkyl-A-CH₂CH₂-Phe-(2-F-Phe)-Heptoxy
Alkyl-A-CH₂CH₂-Phe-(2-F-Phe)-Octoxy
Alkyl-A-CH₂CH₂-Phe-(2-F-Phe)-Nonoxy
Alkyl-A-CH₂CH₂-Phe-(2-F-Phe)-Decoxy (XXXVI)

Alkyl-A-CH₂O-Phe-Pyr-Methyl
Alkyl-A-CH₂O-Phe-Pyr-Ethyl
Alkyl-A-CH₂O-Phe-Pyr-Propyl
Alkyl-A-CH₂O-Phe-Pyr-Butyl
Alkyl-A-CH₂O-Phe-Pyr-Pentyl
Alkyl-A-CH₂O-Phe-Pyr-Hexyl
Alkyl-A-CH₂O-Phe-Pyr-Heptyl
Alkyl-A-CH₂O-Phe-Pyr-Octyl
Alkyl-A-CH₂O-Phe-Pyr-Nonyl
Alkyl-A-CH₂O-Phe-Pyr-Decyl (XXXVII)

Alkyl-A-CH₂CH₂-Cyc-CN
Alkyl-A-CH₂CH₂-Cyc-Methyl
Alkyl-A-CH₂CH₂-Cyc-Ethyl
Alkyl-A-CH₂CH₂-Cyc-Propyl
Alkyl-A-CH₂CH₂-Cyc-Butyl
Alkyl-A-CH₂CH₂-Cyc-Pentyl
Alkyl-A-CH₂CH₂-Cyc-Hexyl
Alkyl-A-CH₂CH₂-Cyc-Heptyl
Alkyl-A-CH₂CH₂-Cyc-Octyl
Alkyl-A-CH₂CH₂-Cyc-Nonyl
Alkyl-A-CH₂CH₂-Cyc-Decyl The compounds of the formula I are prepared by methods known per se as they are described in the literature (e.g. in standard works such as Houben-Weyl, Methoden der Organischen Chemie (Methods of Organic Chemistry), Georg-Thieme Verlag, Stuttgart), and in fact under reaction conditions which are known and suitable for the said reactions. In this connection use can also be made of variations known per se and not mentioned in more detail here.

The starting substances may, if desired, be formed in situ in such a manner that they are not isolated from the reaction mixture but are immediately converted further into the compounds of the formula I.

Thus, the compounds of the formula I may be prepared by reducing a compound which in other respects corresponds to the formula I but contains instead of H atoms one or more reducible groups and/or C-C bonds.

As reducible groups carbonyl groups are particularly suitable, in particular keto groups, and also, for example, free or esterified hydroxy groups or aromatically bonded halogen atoms. Preferred starting substances for the reduction correspond to the formula I, but may contain instead of a cyclohexane ring a cyclohexene ring or cyclohexanone ring and/or instead of a —CH₂CH₂— group a —CH=CH— group and/or instead of a —CH₂— group a —CO— group and/or instead of an H atom a free or a functionally (e.g. in the form of its p-toluenesulphonate) modified OH group.

The reduction may, for example, take place by catalytic hydrogenation at temperatures between 0° and about 200° C. and also pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. As catalysts noble metals such as Pt or Pd are expediently suitable which may be used in the form of oxides (e.g. PtO₂, PdO), on a carrier (e.g. Pd on carbon, calcium carbonate or strontium carbonate) or in finely divided form.

Ketones may also be reduced by the Clemmensen method (with zinc, amalgamated zinc or tin and hydrochloric acid, expediently in aqueous-alcoholic solution or in a heterogeneous phase with water/toluene at temperatures between around 80° and 120°) or the Wolff-Kishner method (with hydrazine, expediently in the presence of alkali such as KOH or NaOH in a high-boiling solvent such as diethylene glycol or triethylene glycol at temperatures between about 100° and 200°) to the corresponding compounds of the formula I which contain alkyl groups and/or —CH₂CH₂— bridges.

In addition, reductions using complex hydrides are possible. For example, arylsulphonyloxy groups may be removed by reduction with LiAlH₄, in particular p-toluenesulphonyloxymethyl groups may be reduced to methyl groups, expediently in an inert solvent such as diethyl ether or THF at temperatures between about 0° and 100°. Double bonds may (even in the presence of CN groups) be hydrogenated with NaBH₄ or tributyltin hydride to methanol.

Particularly advantageously the compounds of the formula I are obtained by cyclization of carboxylic acid amides or thiocarboxylic acid amides with a 2-substituted 1,3-dihalopropane or a 2-substituted 3-halopropylamine. Cyclization of amides leads to dihydro-1,3(4H)-oxazines of the formula I, cyclization of thioamides leads to dihydro-1,3(4H)-thiazines of the formula I.

The amides used as starting substances can be obtained by methods known per se, e.g. from carboxylic acids or their reactive derivatives, by reaction with ammonia as described, for example, in Houben-Weyl, Methoden der Organischen Chemie (Methods of Organic Chemistry), volume VIII, Georg-Thieme Verlag, Stuttgart. As reactive carboxylic acid derivatives acid chlorides or anhydrides, esters or nitriles, for example, may be used. Thioamides may be obtained, for example, from nitriles using hydrogen sulphide.

The preparation of the partly known 2,3-disubstituted propylamines used as starting substances takes place, for example, from 2-substituted 1,3-propanediols or from 2-substituted 3-aminopropanols which are in turn accessible, for example, by reduction of the corresponding carboxylic acids or their derivatives and which are converted by standard processes of organic chemistry into the halo compounds concerned.

The reactants are cyclized with one another without solvent or expediently in the presence of an inert solvent.

Preferably, alcohols such as methanol, ethanol, isopropanol, n-butanol, isoamyl alcohol, glycol and ethers thereof such as ethylene glycol, diethylene glycol, ethylene glycol monomethyl or monoethyl ether (methylglycol or ethylglycol), and also ethers such as tetrahydrofuran, dioxane or ethylene glycol dimethyl ether (diglyme), and also amides such as dimethyl formamide, hexamethylphosphoric triamide, dimethyl acetamide or N-methylpyrrolidone, and also sulphoxides such as dimethyl sulphoxide or sulpholane and also hydrocarbons such as pentane, hexane, cyclohexane, benzene or toluene are suitable as inert solvents. The reaction temperatures are usually between 0° C. and the boiling point of the solvent, preferably between about 50° C. and 150° C. The starting substances may be reacted together without the addition of a further reactant, but the presence of a base is expedient in order to remove the hydrogen halide produced. Alkali metal amides, alkali and alkaline earth hydroxides, carbonates and hydrogencarbonates and also ammonia, strong organic bases and basic ion exchangers are examples of suitable bases. Preferred bases are alkali hydroxides and organic bases, in particular potassium and sodium hydroxide, pyridine and triethylamine.

In a further advantageous process a 2-substituted N-acyl-3-hydroxypropylamine may be cyclized with a base or phosphorous pentasulphide or a 2-substituted N-acyl-3-mercaptopropylamine may be cyclized. The cyclization of amides of this type may be carried out under the same reaction conditions as described for the reaction of amides and thioamides with halopropanes using the same bases and solvents.

The N-acylpropylamines used as starting substances can be obtained, for example, by the methods known per se for the preparation of carboxylic acid amides (as described, for example, in Houben-Weyl, Methoden der organischen Chemie (Methods of Organic Chemistry), volume VIII, Georg-Thieme Verlag, Stuttgart) from the corresponding amines using carboxylic acids or their reactive derivatives.

Esters of the formula I can also be obtained by esterification of corresponding carboxylic acids (or their reactive derivatives) with alcohols or phenols (or their reactive derivatives).

The acid halides, in particular the chlorides and bromides, and also the anhydrides, e.g. also mixed anhydrides, azides or esters, in particular alkyl esters with 1–4 C atoms in the alkyl group, are particularly suitable as reactive derivatives of the said carboxylic acids.

As reactive derivatives of the said alcohols or phenols, in particular the corresponding metal alcoholates or phenolates, preferably of an alkali metal such as Na or K, are suitable.

The esterification is advantageously carried out in the presence of an inert solvent. Well suited are in particular ethers such as diethyl ether, di-n-butyl ether, THF, dioxane or anisole, ketones such as acetone, butanone or cyclohexanone, amides such as DMF or hexamethylphosphoric triamide, hydrocarbons such as benzene, toluene or xylene, halohydrocarbons such as carbon tetrachloride or tetrachloroethylene and sulphoxides such as dimethyl sulphoxide or sulpholane. Solvents immiscible with water may at the same time advantageously be used for the azeotropic distilling off of the water formed during the esterification. Occasionally an excess of an organic base, e.g. pyridine, quinoline or triethylamine may be used as the solvent for the esterification. The esterification may also be carried out in the absence of a solvent, e.g. by simply heating the components in the presence of sodium acetate. The reaction temperature is usually between $-50°$ and $+250°$, preferably between $-20°$ and $+80°$ C. At these temperatures, the esterification reactions are as a rule complete after 15 minutes to 48 hours.

In detail, the reaction conditions for the esterification essentially depend on the nature of the starting substances used. Thus, a free carboxylic acid is reacted with a free alcohol or phenol as a rule in the presence of a strong acid, for example a mineral acid such as hydrochloric acid or sulphuric acid. A preferred manner of reaction is the reaction of an acid anhydride or in particular an acid chloride with an alcohol, preferably in a basic medium, in particular alkali metal hydroxides such as sodium or potassium hydroxide, alkali metal carbonates or hydrogencarbonates such as sodium carbonate, sodium hydrogencarbonate, potassium carbonate or potassium hydrogencarbonate, alkali metal acetates such as sodium or potassium acetate, alkaline-earth metal hydroxides such as calcium hydroxide or organic bases such as triethylamine, pyridine, lutidine, collidine or quinoline are of importance as bases. A further preferred embodiment of the esterification consists in first converting the alcohol or the phenol into the sodium or potassium alcoholate or phenolate respectively, e.g. by treatment with ethanolic sodium or potassium hydroxide, isolating it and suspending it, with stirring, together with sodium hydrogen-carbonate or potassium carbonate in acetone or diethyl ether and mixing this suspension with a solution of the acid chloride or anhydride in diethyl ether, acetone or DMF, expediently at temperatures between about $-25°$ and $+20°$.

For the manufacture of nitriles of the formula I (in which $R^1$ and/or $R^2$ denotes CN and/or in which $A^2$, $A^3$ and/or $A^4$ is substituted by at least one CN group) corresponding acid amides, for example those in which a $CONH_2$ group replaces the radical X, may be dehydrated. The amides are, for example, obtainable from corresponding esters or acid halides by reaction with ammonia. As water-eliminating agents inorganic acid chlorides such as $SOCl_2$, $PCl_3$, $PCl_5$, $POCl_3$, $SO_2Cl_2$, $COCl_2$, and also $P_2O_5$, $P_2S_5$, $AlCl_3$ (e.g. as a double compound with NaCl), aromatic sulphonic acids and sulphonic acid halides are, for example, suitable. In these processes it is possible to work in the presence or absence of an inert solvent at temperatures between about 0° and 150°; as solvents bases such as pyridine or triethylamine, aromatic hydrocarbons such as benzene, toluene—or xylene or amides such as DMF are, for example, suitable.

To prepare the abovenamed nitriles of the formula I corresponding acid halides, preferably the chlorides, may also be reacted with sulphamides, expediently in an inert solvent such as tetramethylenesulphone at temperatures between about 80° to 150°, preferably at 120°. After the usual working up the nitriles can be isolated directly.

Ethers of the formula I (in which $R^1$ and/or $R^2$ and/or $R^3$ denote an alkoxy group and/or in which $Z^1$ and/or $Z^2$ is a $-OCH_2-$ or a $-CH_2O-$ group) are obtainable by etherification of corresponding hydroxy compounds, preferably corresponding phenols, the hydroxy compound expediently first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This derivative can then be reacted with the corresponding alkyl halide, sulphonate or dialkyl sulphate, expediently in an inert solvent such as acetone, 1,2-dimethoxyethane, DMF or dimethyl sulphoxide or also an excess of aqueous or aqueous-alcoholic NaOH or KOH at temperatures between about 20° and 100°.

For the preparation of nitriles of the formula I (in which $R^1$ and/or $R^2$ denote CN and/or in which $A^2$, $A^3$ and/or $A^4$ is substituted by at least one CN group) corresponding chloro or bromo compounds of the formula I (in which $R^1$ and/or $R^2$ denote (Cl or Br and/or in which A is substituted by at least one Cl or Br atom) may also be reacted with a cyanide, expediently with a metal cyanide such as NaCN, KCN or $Cu_2(CN)_2$, for example in the presence of pyridine in an inert solvent such as DMF or N-methylpyrrolidone at temperatures between 20° and 200°.

Compounds of the formula I in which $R^1$ and/or $R^2$ and/or $R^3$ denote F, Cl, Br or CN may also be obtained from the corresponding diazonium salts by exchanging the diazonium group for a fluorine, chlorine or bromine atom or for a CN group, for example by the Schiemann or Sandmeyer methods.

The diazonium salts can be prepared, for example, by nitration of compounds which correspond to the formula I but contain one (or two) hydrogen atom(s) instead of the radicals $R^1$ and/or $R^2$ and/or $R^3$, reduction to the corresponding amines and diazotization, for example, with $NaNO_2$ or $KNO_2$ in aqueous solution at temperatures between $-10°$ and $+10°$.

To exchange the diazonium group for fluorine diazotization may be carried out in anhydrous hydrofluoric acid followed by heating, or conversion is carried out to the diazonium tetrafluoroborates with tetrafluoroboric acid followed by thermal decomposition.

An exchange for Cl, Br or CN is expediently achieved—by reaction of the aqueous diazonium salt solution with $Cu_2Cl_2$, $Cu_2Br_2$ or $Cu_2(CN)_2$ by the Sandmeyer method.

A base of the formula I can be converted with an acid into the respective acid addition salt. For this reaction inorganic acids may be used, for example sulphuric acid, nitric acid, hydrogen halide acids such as hydrochloric acid or hydrobromic acid, phosphoric acids such as orthophosphoric acid, sulphamic acids, and also organic acids, in particular aliphatic, alicyclic, araliphatic, aromatic or heterocyclic mono- or multibasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane or ethanesulphonic acid, ethanedisulphonic acid, 2-hydroxyethanesulphonic acid, benzenesulphonic acid, p-toluenesulphonic acid, naphthalene-mono- and disulphonic acids, and laurylsulphuric acid.

Conversely, it is possible to liberate the base of the formula I from an acid addition salt of a compound of the formula I by treatment with a base, for example with a strong inorganic base such as KOH or NaOH. Thus, the salts of this invention are useful at least to prepare the corresponding bases.

The liquid crystalline phases according to the invention comprise 2 to 25, preferably 3 to 15 components, including at least one compound of the formula I. The other components are preferably selected from the nematic or nematogeneous substances, in particular the known substances from the classes of the azoxybenzenes, benzylideneanilines, biphenyls, terphenyls, phenyl or cyclohexyl benzoate, phenyl or cyclohexyl cyclohexanecarboxylate, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenyl- or cyclohexylpyrimidines, phenyl- or cyclohexyldioxanes, phenyl- or cyclohexyldithianes, 1,2-bisphenylethane, 1,2-biscyclohexylethanes, 1-phenyl-2-cyclohexylethanes, optionally halogenated stilbenes, benzyl phenyl ether, tolans and substituted cinnamic acids.

The most important compounds suitable as components of liquid crystalline phases of this type can be characterised by the formula II

in which L and E each denote a carbo- or heterocyclic ring system from the group formed from 1,4-disubstituted benzene and cyclohexane rings, 4,4'-disubstituted biphenyl systems, phenylcyclohexane systems and cyclohexylcyclohexane systems, 2,5-disubstituted pyrimidine and 1,3-dioxane rings, 2,6-disubstituted naphthalene, di and tetrahydronaphthalene, quinazoline and tetrahydroquinazoline:

| -continued | |
|---|---|
| —CO—O— | —CH₂—O— |
| —CO—S— | —CH₂—S— |
| —CH=N— | —COO—Phe—COO— | or denotes a C—C single bond, y denotes halogen, preferably chlorine, or —CN, and R' and R" denote alkyl, alkoxy, alkanoyloxy or alkoxycarbonyloxy having up to 18, preferably up to 8 carbon atoms, denotes one of these radicals denotes also for CN, NC, NO$_2$, CF$_3$, F, Cl or Br.

In most of these compounds R' and R" are different from each other, one of these radicals usually being an alkyl or alkoxy group. But other variations of the substituents provided are common. Many such substances or also mixtures thereof are obtainable commercially. All of these substances can be prepared by methods known in the literature.

The liquid crystalline phases according to the invention contain about 0.1 to 99, preferably 10 to 95%, of one or more compounds of the formula I. Also preferred are liquid crystalline phases which contain 0.1–50, in particular 0.5–30% of one or more compounds of formula I. Isotropic compounds of the formula I can also be used in the phases according to the invention.

The preparation of the liquid crystalline phases according to the invention takes place in the usual manner. As a rule the components are dissolved in each other, expediently at elevated temperature.

The liquid crystalline phases according to the invention can be modified by suitable additives in a manner such that they can be used in all the types of liquid crystal display elements which have hitherto become known.

Such additives are known to the specialist and described comprehensively in the literature. For example conducting salts, preferably ethyldimethyldodecylammonium 4-hexyloxybenzoate, tetrabutylammonium tetraphenylboranate or complex salts of crown ethers (cf. e.g. I. Haller et al., Mol. Cryst. Liq. Cryst., volume 24, pages 249–258 (1973)) may be added to improve the conductivity, dichroic dye-stuffs to prepare colored guest-host systems or substances to modify the dielectric anisotropy, the viscosity and/or the orientation of the nematic phases. Substances of this type are described for example in the German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

M=melting point.

C=clear point.

"Usual processing" means that water is added, extraction with methylene chloride is carried out, separation is carried out, the organic phase is dried, the product is concentrated by evaporation and purified by crystallization and/or chromatography.

EXAMPLE 1

2.4 g of 4-n-hexyloxythiobenzamide (obtainable from 4-n-hexyloxybenzamide by reaction with phosphorous pentasulphide) and 2.7 g of 2-n-pentyl-1,3-dibromopropane (obtainable by reaction of the corresponding diol with 48 percent hydrogen bromide in the presence of concentrated sulphuric acid) are heated together at 120°. After 2 hours they are allowed to cool, mixed with dilute sodium hydroxide and extracted with ether. After evaporating off the solvent and crystallization from isopropanol 2-(4-hexyloxyphenyl)-5(4H)-pentyl-5,6-dihydro-1,3-thiazine is obtained as colorless crystals. M: 37°, C: 51°.

The compounds denoted in the groups I, II, VIII, IX, XIII and XIV are obtained in an analogous manner thereto.

2-(4-bromophenyl)-4H-5-pentyl-5,6-dihydro-1,3-thiazine; m: 53°, k: 0°. 2-(4-nitrophenyl)-4H-5-pentyl-5,6-dihydro-1,3-oxazine; m: 55°, k: 68°

EXAMPLE 2

1.7 g of 4-propylcyclohexanecarboxylic acid amide (obtainable from 4-propylcyclohexanecarboxylic acid using thionyl chloride via the acid chloride and the reaction thereof with ammonia) and 2.8 g of 2-hexyl-1,3-dibromopropane (obtainable from the corresponding diol as specified in Example 1) are heated for 4 hours at 120°. After cooling alkalization is carried out with sodium hydroxide and extraction is carried out with ether. After evaporating off the solvent and crystallization 2-(4-propylcyclohexyl)-5(4H)-hexyl-5,6-dihydro-1,3-oxazine is obtained.

The compounds denoted in the groups III–VII and X–XII are obtained in an analogous manner.

2-(4-(4-propylcyclohexyl)-phenyl)-4H-5-pentyl-5,6-dihydro-1,3-thiazine; m: 102°, k: 142°. 2-(4-(4-pentylcyclohexyl)-cyclohexyl)4H-5-pentyl-5,6-dihydro-1,3-oxazine, m: 94°, k: 143°.

EXAMPLE 3

3.1 g of 4-(4-pentylcylohexyl)bromobenzene (obtainable from the corresponding cyclohexylbenzene by bromination) and 2.8 g of 2-propyl-5(4H)-(4-bromophenyl)-5,6-dihydro-1,3-oxazine (obtainable from 2-(4-bromophenyl)malonate by reduction and conversion of the diol as in Example 1 to 2-(4-bromophenyl)-1,3-dibromopropane and reaction of the latter with butyramide) are heated at 160° C. for 14 hours after adding 1 g of copper bronze. The reaction mixture is then taken up in ether, filtered off from the insoluble material and concentrated to the residue. After chromatographic purification 2-propyl-5(4H)-(4'-(4-pentylcyclohexyl)-biphenyl-4-yl)-5,6-dihydro-1,3-oxazine is obtained.

EXAMPLE 4

In accordance with Example 2, 3.0 g of 2-heptyl-1,3-bromopropane (obtained from 2-heptylmalonic ester by reduction and reaction in accordance with Example 1) and 1.8 g of 2-propylpyrimidine-5-carboxylic acid thioamide (obtained from the corresponding carboxylic acid amide using phosphorous pentasulphide) are made to react. In this manner 2-(2-propylpyrimidin-5-yl)-5(4H)-heptyl-5,6-dihydro-1,3-oxazine is obtained.

The compounds deoted in group XVI and XVII are obtained in an analogous manner.

EXAMPLE 5

2.0 g of 5-pentyl-5,6(4H)-dihydro-1,3-oxazine-2-carboxylic acid (obtainable from 2-pentyl-1,3-dibromopropane using oxalamide ester analogously to Example 1 and subsequent saponification) are converted to the acid chloride by heating with 1.5 g of thionyl chloride. Concentration by evaporation is carried out, the residue is dissolved in 20 ml of toluene, mixed with 1.5 ml of pyridine and 1.2 g of 4-cyanophenol and boiled for 3 hours. The mixture is mixed with water. Separation is carried out, the organic phase is washed with water, dried over sodium sulphate, concentration by evaporation is carried out and 4-cyanophenyl 5(4H)-pentyl-5,6-dihydro-1,3-oxazine-2-carboxylate is obtained.

The compounds denoted in the groups XVIII–XXI are obtained in an analogous manner.

EXAMPLE 6

3.2 g of 2-(4-carboxyphenyl)-5(4H)-heptyl-5,6-dihydro-1,3-thiazine (prepared from terephthalthioamic acid and 2-heptyl-1,3-dibromopropane analogously to Example 1) are converted to the acid chloride as specified in Example 5 and esterified with 1.7 g of 4-butoxyphenol. 4-butoxyphenyl 4-(5(4H)-heptyl-5,6-dihydro-1,3-thiazin-2-yl)-benzoate is obtained.

The compounds specified in the groups XXII–XXIV and XXVI–XXVIII are obtained in an analogous manner.

EXAMPLE 7

The solution of 3.5 g 1-(5(4H)-pentyl-5,6-dihydro-1,3-oxazin-2-yl)-2-(4'-ethylbiphenyl-4-yl)-ethene (prepared from ethyl 5(4H)-pentyl-5,6-dihydro-1,3-oxazine-2-carboxylate after reduction to the alcohol, oxidation with manganese(IV) oxide to the aldehyde and Wittig reaction of the latter with triphenyl-4'-ethylbiphenyl-4-ylmethylenephosphorane) in 50 ml of methanol is shaken at 20° at atmospheric pressure with hydrogen after addition of 0.5 g of 5% palladium/active charcoal catalyst. After 2 hours the hydrogen absorption has stopped, whereupon filtration from the catalyst is carried out. The solvent is evaporated off under reduced pressure and the residue is recrystallized. In this way 1-(5(4H)-pentyl-5,6-dihydro-1,3-oxazin-2-yl)-2-(4'-ethylbiphenyl-4-yl)-ethane is obtained.

The compounds specified in the groups XXXIII–XXXV and XXXVII are obtained in an analogous manner.

EXAMPLE 8

1.85 g of 2-hydroxymethyl-5(4H)-pentyl-5,6-dihydro-1,3-oxazine obtained as in Example 7 are dissolved in 25 ml of benzene and treated with phosphorous tribromide at 20°. After decanting off the phosphorous acid obtained the reaction solution is concentrated to produce a residue and dissolved in 40 ml of dimethyl formamide. 1.0 g of 2-heptyl-5-(4-hydroxyphenyl)pyrimidine and 2 ml of triethylamine are added and stirring is then carried out for 6 hours at 20° C. For the working up the solution is poured onto 250 ml of water and extracted with ether. After washing the extract with water and drying over sodium sulphate concentration is carried out and the residue is recrystallized.

In this way 2-{4-(2-heptylpyrimidin-5-yl)phenoxymethyl}-5(4H)-phenyl-5,6-dihydro-1,3-oxazine is obtained.

The compounds specified in group XXXVII are obtained in an analogous manner.

There follow examples of the mixtures according to the invention.

EXAMPLE A

A mixture is prepared from
- 24%: 2-(4-butoxyphenyl)-5(4H)-pentyl-5,6-dihydro-1,3-oxazine
- 15%: trans-4-(4-propylcyclohexyl)benzonitrile
- 25%: trans-4-(4-pentylcyclohexyl)benzonitrile
- 14%: trans-4-(4-ethoxyphenyl)propylcyclohexane
- 12%: trans-4-(4-butoxyphenyl)propylcyclohexane
- 10%: 4-(trans-4-pentylcyclohexyl)-4'-(trans-4-propylcyclohexyl)biphenyl

EXAMPLE B

A mixture is prepared from
- 19%: 2-(4-cyanophenyl)-5(4H)-5,6-dihydro-1,3-thiazine
- 16%: 2-(4-ethylphenyl)-5-propyl-1,3-dioxane
- 12%: 2-(4-butoxyphenyl)-5-propyl-1,3-dioxane
- 13%: trans-4-(4-hexylphenyl)ethylcyclohexane
- 18%: 4-butyl-4'-cyanobiphenyl
- 15%: trans-4-{4-(4-pentylcyclohexyl)cyclohexyl}benzonitrile
- 7%: trans-4-{4-(4-pentylcyclohexyl)cyclohexyl}cyanocyclohexane

EXAMPLE C

A mixture is prepared from
- 29%: trans-2-(4-cyanocyclohexyl)-5(4H)-heptyl-1,3-oxazine
- 25%: trans-2-(4-cyanocyclohexyl)-5(4H)-pentyl-1,3-thiazine
- 15%: 4-ethoxyphenyl trans-4-propylcyclohexanecarboxylate
- 14%: 4-propylcyclohexyl trans-4-butylcyclohexanecarboxylate
- 10%: 4-(4-propylcyclohexyl)phenyl trans-4-butylcyclohexanecarboxylate
- 7%: 4-(5-heptyl-1,3-dioxan-2-yl)benzonitrile

EXAMPLE D

A mixture is prepared from
- 27%: 4-propylphenyl 4-(5(4H)-pentyl-5,6-dihydro-1,3-thiazin-2-yl)benzoate
- 21%: trans-2-(4-cyanocyclohexyl)-5-butyl-1,3-dioxane
- 18%: trans-2-(4-butanoyloxycyclohexyl)-5-butyl-1,3-dioxane 18%: trans-2-(4-hexylcyclohexyl)-2-fluorobenzonitrile
16%: 4-(4-ethylphenoxycarbonyl)phenyl 4-heptylbenzoate

EXAMPLE E

A mixture is prepared from
24%: 4-propylcyclohexyl trans-4-(5(4H)-pentyl-5,6-dihydro-1,3-oxazin-2-yl)carboxylate
19%: 4-propylcyclohexyl trans-4-(5(4H)-pentyl-5,6-dihydro-1,3-thiazin-2-yl)cyclohexanecarboxylate
15%: 4-propylcyclohexyl trans-(4-(4-pentylcyclohexyl)cyclohexanecarboxylate
15%: 4-cyanophenyl trans-4-heptylcyclohexanecarboxylate
15%: 4-cyanophenyl butoxybenzoate
12%: 4-(4-hexylcyclohexyl)cyanocyclohexane

EXAMPLE F

A mixture is prepared from
28%: 4-cyanophenyl 4-(5(4H)-pentyl-5,6-dihydro-1,3-thiazin-2-yl)benzoate
26%: 4-cyanophenyl 4-(5(4H)-propyl-5,6-dihydro-1,3-thiazin-2-yl)benzoate
16%: 4-pentylphenyl 4-methoxybenzoate
1.2%: 4-propylphenyl 4-(4-pentylcyclohexyl)benzoate
12%: 4-fluorophenyl 4-(4-butylcyclohexyl)benzoate
6%: 1-{4-(4-butylcyclohexyl)cyclohexyl}-2-(4-hexylcyclohexyl)ethane

EXAMPLE G

A mixture is prepared from
32%: 2-(4-hexoxyphenyl)-5(4H)-pentyl-5,6-dihydro-1,3-thiazine
24%: 2-(4-butoxyphenyl)-5-pentylpyrimidine
22%: 2-(4-propylcyclohexyl)-5-heptyl-1,3-dioxane
17%: 4-cyanophenyl 4-(4-hexylcyclohexyl)benzoate
5%: 1-cyano-1-(4-butylcyclohexyl)-2-(4-hexylcyclohexyl)ethane

EXAMPLE H

A mixture is prepared from
24%: 4-cyanocyclohexyl 4-(5(4H)-heptyl-5,6-dihydro-1,3-oxazin-2-yl)cyclohexanecarboxylate
21%: 4-cyanocyclohexyl 4-(5(4H)-pentyl-5,6-dihydro-1,3-oxazin-2-yl)cyclohexanecarboxylate
18%: 2-(4-propoxycyclohexyl)-5-pentyl-1,3-dioxane
15%: 2-(4-cyanophenyl)-5-hexylpyrimidine
12%: 4-{4-(4-propoxycyclohexyl)cyclohexyl}-heptylcyclohexane
5%: 3-fluoro-4-cyanophenyl 4-butylbenzoate
5%: 1-(4-butylcyclohexyl)-2-{4-(4-hexylcyclohexyl)biphenyl-4-yl}ethane

EXAMPLE I

A mixture is prepared from
28%: 2-(4-propoxycyclohexyl)-5(4H)-pentyl-5,6-dihydro-1,3-oxazine
28%: 2-(4-propoxycyclohexyl)-5(4H)-pentyl-5,6-dihydro-1,3-thiazine
21%: 4-(4-propoxycyclohexyl)pentylcyclohexane
9%: 2-(4-cyanophenyl)-5-(4-butylcyclohexyl)pyrimidine
8%: 4-cyano-4'-(4-propylcyclohexyl)biphenyl
6%: 4-{4-(3-fluoro-4-cyanophenyl)cyclohexyl}butylcyclohexane

EXAMPLE J

A mixture is prepared from
33%: 2-(4-propylcyclohexyl)-5(4H)-pentyl-5,6-dihydro-1,3-oxazine
25%: 4-(4-propylcyclohexyl)pentylcyclohexane
17%: 2-(4-cyanophenyl)-5-(4-ethylphenyl)pyrimidine
10%: 1-(4-pentylcyclohexyl)-2-(4-propylcyclohexyl)ethane
9%: 4-propylcyclohexyl 1-cyano-4-pentylcyclohexane-1-carboxylate
6%: 2-fluoro-4-(4-heptycyclohexyl)-4'-(4-pentylcyclohexyl)biphenyl

EXAMPLE K

A mixture is prepared from:
36%: 2-(4-heptylcyclohexyl)-5(4H)-propyl-5,6-dihydro-1,3-oxazine
22%: 4-heptyl-4'-(4-ethylcyclohexyl)biphenyl
15%: 2-(4-butoxyphenyl)-5-(4-ethylcyclohexyl)pyrimidine
13%: 4-(4-pentanoyloxycyclohexyl)propylcyclohexane
7%: 1-cyano-1-(4-butylcyclohexyl)-4-(4-ethylcyclohexyl)cyclohexane
7%: 1-(4-propylcyclohexyl)-2-4-(4-cyanophenyl)cyclohexyl ethane

EXAMPLE L

A mixture is prepared from:
34%: 2-(4-butoxyphenyl)-5(4H)-pentyl-5,6-dihydro-1,3-oxazine
24%: 4-(methoxy-4'-(4-heptylcyclohexyl)biphenyl
21%: 1-(4-propylcyclohexyl)-2-(2'-fluoro-4'-pentyl-biphenyl-4-yl)ethane
15%: 4-hexylphenyl 1-cyano-4-ethylcyclohexanecarboxylate
6%: 2,3-dicyano-4-pentylphenyl 4-propylcyclohexanecarboxylate

EXAMPLE M

A mixture is prepared from:
21%: 2-(4-cyanophenyl)-5(4H)-butyl-5,6-dihydro-1,3-oxazine
19%: 4-pentylphenyl 4-(5(4H)-propyl-5,6-dihydro-1,3-oxazin-2-yl)benzoate
18%: 4-pentylphenyl trans-4-propylcyclohexanecarboxylate
17%: 2-(4-pentylcyclohexyl)-5(4H)-ethyl-5,6-dihydro-1,3-oxazine
15%: 4-heptylphenyl 4-(5(4H)-propyl-5,6-dihydro-1,3-thiazin-2-yl)benzoate
10%: 4'-heptyl-4-cyanobiphenyl

EXAMPLE N

A mixture is prepared from:
38%: trans-4-(4-cyanophenyl)pentylcyclohexane
15%: 2-(4-cyanophenyl)-5(4H)-propyl-5,6-dihydro-1,3-oxazine
16%: 2-(4-cyanophenyl)-5(4H)-pentyl-5,6-dihydro-1,3-oxazine
19%: 2-(4-cyanophenyl)-5(4H)-hexyl-5,6-dihydro-1,3-oxazine
12%: trans-4-(4-cyanobiphenyl-4'-yl)-pentylcyclohexane The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid crystalline phase comprising at least two liquid crystalline components at least one of which is a 5,6-dihydroazine derivative of the formula $R^1-A^1-Z^1-A^2-R^2$ wherein
each of $R^1$ and $R^2$ independently is alkyl of 1-15 C atoms, or alkyl of 1-15 C atoms in which one or two nonadjacent CH$_2$ groups are replaced by —O—, —CO—, —O—CO—, —CO—O— or —CH=CH—, and one of $R^1$ and $R^2$ can also be H, F, Cl, Br, CN, or $R^3-A^3-Z^2$, $A^1$ is —A—, —A$^4$—A—, or —A—A$^4$—, A is

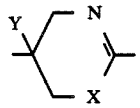

X is O or S,
Y is H, C$_1$-C$_4$-alkyl, F, Cl, Br, or CN,
each of A$^2$, A$^3$ and A$^4$ independently is a 1,4-cyclohexylene, 1,3-dioxane-2,5-diyl or a 1,3-dithiane-2,5-diyl group; is one of said three groups substituted, respectively, in the 1- or 4-, 2- or 5-, or 2- or 5-position, by C$_1$-C$_4$-alkyl, F, Cl, Br, CF$_3$, or CN; is a piperidine-1,4-diyl, 1,4-bicyclo-[2.2.2]-octylene A or 1,4-phenylene group; or is a 1,4-phenylene group substituted by one or two F, Cl, CH$_3$ or CN groups, or one of said phenylene groups in which one or two CH groups may also be replaced by N;
each of Z$^1$ and Z$^2$ independently is —CO—O—, —O—CO—, —CH$_2$CH$_2$—, —CHCN—CH$_2$—, —CH$_2$—CHCN—, —CH=CH—, —OCH$_2$—, —CH$_2$O—, —CH=N—, —N=CH—, —NO=N—, —N=NO— or a single bond and
$R^3$ is alkyl of 1-15 C atoms, alkyl of 1-15 C atoms in which one or two nonadjacent CH$_2$ groups are replaced by —O—, —CO—, —O—CO—, —CO—O— or —CH=CH—, or H, F, Cl, Br, or CN, and wherein all substituted and unsubstituted rings are selected from Cy: a 1,4-cyclohexylene group, Oaz: a 5,6-dihydro-1,3(4H)-oxazine-2,5-diyl group, Taz: a, 5,6-dihydro-1,3-(4H)-thiazine-2,5-diyl group, Dio: a 1,3-dioxane-2,5-diyl group, Dit: a 1,3-dithiane-2,5-diyl group, Bi: a bicyclo[2.2.2]octylene group, Pip: a piperidine-1,4-diyl group, Phe: a 1,4-phenylene group, Pyr: a pyrimidine-2,5-diyl group or Pyn: a pyridazine-3,6-diyl group.

2. A phase of claim 1 wherein said derivative is of the formula
$R^1-A-Z^1-A^2-R^2$ or
$R^1-A-A^2-R^2$.

3. A phase of claim 1 wherein said derivative is
$R^1-A^4-A-Z^1-A^2-R^2$
$R^1-A-A^4-Z^1-A^2-R^2$
$R^1-A-Z^1-A^2-Z^2-A^3-R^3$
$R^3-A^3-Z^2-A-Z^1-A^2-R^2$
$R^1-A-Z^1-A^2-A^3-R^2$
$R^1-A-A^2-Z^2-A^3-R^3$
$R^3-A^3-Z^2-A-A^2-R^2$
$R^3-A^3-A-Z^1-A^2-R^2$
$R^1-A^4-A-A^2-R^2$ or
$R^1-A-A^4-A^2-R^2$.

4. A phase of claim 1 wherein said derivative is
$R^3-A^3-Z^2-A-Z^1-A^2-Z^2-A^3-R^3$
$R^3-A^3-A-Z^1-A^2-A^3-R^3$
$R^3-A^3-Z^2-A-A^2-A^3-R^3$
$R^3-A^3-A-A^2-Z^2-A^3-R^3$
$R^1-A^4-A-Z^1-A^2-Z^2-A^3-R^3$
$R^3-A^3-Z^2-A^4-A-Z^1-A^2-R^2$
$R^1-A-A^4-Z^1-A^2-Z^2-A^3-R^3$
$R^3-A^3-Z^2-A-A^4-Z^1-A^2-R^2$
$R^1-A^4-A-A^2-A^3-R^3$
$R^1-A-A^4-A^2-A^3-R^3$
$R^1-A^4-A-A^2-Z^2-A^3-R^3$
$R^1-A^4-A^4-A^2-Z^2-A^3-R^3$
$R^1-A^4-A-Z^1-A^2-A^3-R^3$
$R^1-A-A^4-Z^1-A^2-A^3-R^3$
$R^3-A^3-A^4-A-A^2-R^2$
$R^3-A^3-A-A^4-A^2-R^2$
$R^3-A^3-A^4-A-Z^1-A^2-R^2$
$R^3-A^3-A-A^4-Z^1-A^2-R^2$
$R^3-A^3-Z^2-A^4-A-A^2-R^2$ or
$R^3-A^3-Z^2-A-A^4-A^2-R^2$.

5. A phase of claim 1 wherein said derivative is of the formula
$R^3-A^3-Z^2-A^4-A-Z^1-A^2-Z^2-A^3-R^3$
$R^3-A^3-Z^2-A-A^4-Z^1-A^2-Z^2-A^3-R^3$
$R^3-A^3-A^4-A-A^2-A^3-R^3$
$R^3-A^3-A-A^4-A^2-A^3-R^3$
$R^3-A^3-A^4-A-Z^1-A^2-A^3-R^3$ or
$R^3-A^3-A-A^4-Z^1-A^2-A^3-R^3$.

6. A phase of claim 1 wherein said derivative is of the formula
$R^1$-Oaz-COO-Phe-$R^2$
$R^1$-Oaz-CH$_2$CH$_2$-Phe-$R^2$
$R^1$-Oaz-Phe-COO-Phe-$R^2$
$R^1$-Oaz-Phe-CH$_2$CH$_2$-Phe-$R^2$
$R^1$-Oaz-Phe-CH$_2$CH$_2$-Cy-$R^2$
$R^1$-Oaz-Phe-CH$_2$CH$_2$-Phe-Cy-$R^3$
$R^1$-Oaz-Phe-CH$_2$CH$_2$-Phe-Dio-$R^3$
$R^1$-Oaz-Phe-$R^2$
$R^1$-Oaz-Phe-Phe-$R^2$
$R^1$-Oaz-Phe-Phe-Cy-$R^3$
$R^1$-Oaz-Phe-Phe-Dio-$R^3$
$R^1$-Oaz-Cy-Phe-$R^2$
$R^1$-Cy-Oaz-Phe-$R^2$
$R^1$-Oaz-Cy-$R^3$
$R^1$-Oaz-Cy-Cy-$R^3$
$R^1$-Oaz-Pyr-$R^2$
$R^1$-Oaz-CH$_2$CH$_2$-Phe-Phe-$R^2$
$R^1$-Oaz-CH$_2$CH$_2$-Phe-Phe-Cy-$R^3$
$R^1$-Oaz-CH$_2$CH$_2$-Phe-Cy-$R^2$
$R^1$-Taz-COO-Phe-$R^2$
$R^1$-Taz-CH$_2$CH$_2$-Phe-$R^2$
$R^1$-Taz-Phe-COO-Phe-$R^2$
$R^1$-Taz-Phe-CH$_2$CH$_2$-Phe-$R^2$
$R^1$-Taz-Phe-CH$_2$CH$_2$-Cy-$R^2$
$R^1$-Taz-Phe-CH$_2$CH$_2$-Phe-Cy-$R^3$
$R^1$-Taz-CH$_2$CH$_2$-Phe-Dio-$R^3$
$R^1$-Taz-Phe-$R^2$ R$^1$-Taz-Phe-Phe-R$^2$
R$^1$-Taz-Phe-Phe-Cy-R$^3$
R$^1$-Taz-Phe-Phe-Dio-R$^3$
R$^1$-Taz-Cy-Phe-R$^2$
R$^1$-Cy-Taz-Phe-R$^2$
R$^1$-Taz-Pyr-R$^2$
R$^1$-Taz-CH$_2$CH$_2$-Phe-Phe-R$^2$
R$^1$-Taz-CH$_2$CH$_2$-Phe-Phe-Cy-R$^2$
R$^1$-Taz-CH$_2$CH$_2$-Phe-Cy-R$^2$
R$^1$-Taz-Cy-R$^3$ or
R$^1$-Taz-Cy-Cy-R$^3$.

7. A phase of claim 1, wherein in said derivative —A— is 5,6-dihydro-1,3(4H)-thiazine-2,5diyl or 5,6-dihydro-1,3(4H)-oxazine-2,5-diyl, Phe is 1,4-phenylene, Cy is 1,4-cyclohexylene (Cyc), Dio is 1,3-dioxane-2,5-diyl and Pyr is pyrimidine-2,5-diyl.

8. A phase of claim 7 wherein said derivative is of the formula
Alkyl-A-Phe-CN
Alkyl-A-Phe-Methyl
Alkyl-A-Phe-Ethyl
Alkyl-A-Phe-Propyl
Alkyl-A-Phe-Butyl
Alkyl-A-Phe-Pentyl
Alkyl-A-Phe-Hexyl
Alkyl-A-Phe-Heptyl
Alkyl-A-Phe-Octyl
Alkyl-A-Phe-Nonyl
Alkyl-A-Phe-Decyl
Alkyl-A-Phe-Methoxy
Alkyl-A-Phe-Ethoxy
Alkyl-A-Phe-Propoxy
Alkyl-A-Phe-Butoxy
Alkyl-A-Phe-Pentoxy
Alkyl-A-Phe-Hexoxy
Alkyl-A-Phe-Heptoxy
Alkyl-A-Phe-Octoxy
Alkyl-A-Phe-Nonoxy
Alkyl-A-Phe-Decoxy
Alkyl-A-(3-F-Phe)-CN
Alkyl-A-Cyc-CN
Alkyl-A-Cyc-Methyl
Alkyl-A-Cyc-Ethyl
Alkyl-A-Cyc-Propyl
Alkyl-A-Cyc-Butyl
Alkyl-A-Cyc-Pentyl
Alkyl-A-Cyc-Hexyl
Alkyl-A-Cyc-Heptyl
Alkyl-A-Cyc-Octyl
Alkyl-A-Cyc-Nonyl
Alkyl-A-Cyc-Decyl
Alkyl-A-Cyc-Methoxy
Alkyl-A-Cyc-Ethoxy
Alkyl-A-Cyc-Propoxy
Alkyl-A-Cyc-Butoxy
Alkyl-A-Cyc-Pentoxy
Alkyl-A-Cyc-Hexoxy
Alkyl-A-Cyc-Heptoxy
Alkyl-A-Cyc-Octoxy
Alkyl-A-Cyc-Nonoxy
Alkyl-A-Cyc-Decoxy
Alkyl-A-Cyc-Methoxycarbonyl
Alkyl-A-Cyc-Ethoxycarbonyl
Alkyl-A-Cyc-Propoxycarbonyl
Alkyl-A-Cyc-Butoxycarbonyl
Alkyl-A-Cyc-Pentoxycarbonyl
Alkyl-A-Cyc-Hexoxycarbonyl
Alkyl-A-Cyc-Heptoxycarbonyl
Alkyl-A-Cyc-Octoxycarbonyl
Alkyl-A-Cyc-Nonoxycarbonyl
Alkyl-A-Cyc-Decoxycarbonyl
Alkyl-A-Cyc-Methylcarbonyloxy
Alkyl-A-Cyc-Ethylcarbonyloxy
Alkyl-A-Cyc-Propylcarbonyloxy
Alkyl-A-Cyc-Butylcarbonyloxy
Alkyl-A-Cyc-Pentylcarbonyloxy
Alkyl-A-Cyc-Hexylcarbonyloxy
Alkyl-A-Cyc-Heptylcarbonyloxy
Alkyl-A-Cyc-Octylcarbonyloxy
Alkyl-A-Cyc-Nonylcarbonyloxy
Alkyl-A-Cyc-Decylcarbonyloxy
Methyl-A-Cyc-Oxaalkyl
Ethyl-A-Cyc-Oxaalkyl
Propyl-A-Cyc-Oxaalkyl
Butyl-A-Cyc-Oxaalkyl
Pentyl-A-Cyc-Oxaalkyl
Hexyl-A-Cyc-Oxaalkyl
Heptyl-A-Cyc-Oxaalkyl
Octyl-A-Cyc-Oxaalkyl
Nonyl-A-Cyc-Oxaalkyl or
Decyl-A-Cyc-Oxaalkyl.

9. A phase of claim 7 wherein said derivative is of the formula
Alkyl-A-Phe-Phe-CN
Alkyl-A-Phe-Phe-Methyl
Alkyl-A-Phe-Phe-Ethyl
Alkyl-A-Phe-Phe-Propyl
Alkyl-A-Phe-Phe-Butyl
Alkyl-A-Phe-Phe-Pentyl
Alkyl-A-Phe-Phe-Hexyl
Alkyl-A-Phe-Phe-Heptyl
Alkyl-A-Phe-Phe-Octyl
Alkyl-A-Phe-Phe-Nonyl
Alkyl-A-Phe-Phe-Decyl
Alkyl-A-Phe-(3-F-Phe)-CN
Alkyl-A-Phe-Phe-Methoxy
Alkyl-A-Phe-Phe-Ethoxy
Alkyl-A-Phe-Phe-Propoxy
Alkyl-A-Phe-Phe-Butoxy
Alkyl-A-Phe-Phe-Pentoxy
Alkyl-A-Phe-Phe-Hexoxy
Alkyl-A-Phe-Phe-Heptoxy
Alkyl-A-Phe-Phe-Octoxy
Alkyl-A-Phe-Phe-Nonoxy
Alkyl-A-Phe-Phe-Decoxy
Alkyl-A-Cyc-Phe-CN
Alkyl-A-Cyc-Phe-Methyl
Alkyl-A-Cyc-Phe-Ethyl
Alkyl-A-Cyc-Phe-Propyl
Alkyl-A-Cyc-Phe-Butyl
Alkyl-A-Cyc-Phe-Pentyl
Alkyl-A-Cyc-Phe-Hexyl
Alkyl-A-Cyc-Phe-Heptyl
Alkyl-A-Cyc-Phe-Octyl
Alkyl-A-Cyc-Phe-Nonyl
Alkyl-A-Cyc-Phe-Decyl
Alkyl-A-Cyc-(3-F-Phe)-CN
Alkyl-A-Cyc-Phe-Methoxy Alkyl-A-Cyc-Phe-Ethoxy
Alkyl-A-Cyc-Phe-Propoxy
Alkyl-A-Cyc-Phe-Butoxy
Alkyl-A-Cyc-Phe-Pentoxy
Alkyl-A-Cyc-Phe-Hexoxy
Alkyl-A-Cyc-Phe-Heptoxy
Alkyl-A-Cyc-Phe-Octoxy
Alkyl-A-Cyc-Phe-Nonoxy
Alkyl-A-Cyc-Phe-Decoxy
Alkyl-A-Cyc-Cyc-CN
Alkyl-A-Cyc-Cyc-Methyl
Alkyl-A-Cyc-Cyc-Ethyl
Alkyl-A-Cyc-Cyc-Propyl
Alkyl-A-Cyc-Cyc-Butyl
Alkyl-A-Cyc-Cyc-Pentyl
Alkyl-A-Cyc-Cyc-Hexyl
Alkyl-A-Cyc-Cyc-Heptyl
Alkyl-A-Cyc-Cyc-Octyl
Alkyl-A-Cyc-Cyc-Nonyl
Alkyl-A-Cyc-Cyc-Decyl
Alkyl-Cyc-A-Phe-CN
Alkyl-Cyc-A-Phe-Methyl
Alkyl-Cyc-A-Phe-Ethyl
Alkyl-Cyc-A-Phe-Propyl
Alkyl-Cyc-A-Phe-Butyl
Alkyl-Cyc-A-Phe-Pentyl
Alkyl-Cyc-A-Phe-Hexyl
Alkyl-Cyc-A-Phe-Heptyl
Alkyl-Cyc-A-Phe-Octyl
Alkyl-Cyc-A-Phe-Nonyl
Alkyl-Cyc-A-Phe-Decyl
Alkyl-Cyc-A-(3-F-Phe)-CN
Alkyl-Cyc-A-Phe-Methoxy
Alkyl-Cyc-A-Phe-Ethoxy
Alkyl-Cyc-A-Phe-Propoxy
Alkyl-Cyc-A-Phe-Butoxy
Alkyl-Cyc-A-Phe-Pentoxy
Alkyl-Cyc-A-Phe-Hexoxy
Alkyl-Cyc-A-Phe-Heptoxy
Alkyl-Cyc-A-Phe-Oxtoxy
Alkyl-Cyc-A-Phe-Nonoxy
Alkyl-Cyc-A-Phe-Decoxy
Cyan-Cyc-Phe-Phe-A-Alkyl
Methyl-Cyc-Phe-Phe-A-Alkyl
Ethyl-Cyc-Phe-Phe-A-Alkyl
Propyl-Cyc-Phe-Phe-A-Alkyl
Butyl-Cyc-Phe-Phe-A-Alkyl
Pentyl-Cyc-Phe-Phe-A-Alkyl
Hexyl-Cyc-Phe-Phe-A-Alkyl
Heptyl-Cyc-Phe-Phe-A-Alkyl
Octyl-Cyc-Phe-Phe-A-Alkyl
Nonyl-Cyc-Phe-Phe-A-Alkyl or
Decyl-Cyc-Phe-Phe-A-Alkyl.

10. A phase according to claim 7 wherein said derivative is of the formula
Alkyl-A-Pyr-Methyl
Alkyl-A-Pyr-Ethyl
Alkyl-A-Pyr-Propyl
Alkyl-A-Pyr-Butyl
Alkyl-A-Pyr-Pentyl
Alkyl-A-Pyr-Hexyl
Alkyl-A-Pyr-Heptyl
Alkyl-A-Pyr-Octyl
Alkyl-A-Pyr-Nonyl
Alkyl-A-Pyr-Decyl or
Alkyl-A-Pyr-Phe-CN.

11. A phase of claim 7 wherein said derivative is of the formula
Alkyl-A-COO-Phe-CN
Alkyl-A-COO-Phe-Methyl
Alkyl-A-COO-Phe-Ethyl
Alkyl-A-COO-Phe-Propyl
Alkyl-A-COO-Phe-Butyl
Alkyl-A-COO-Phe-Pentyl
Alkyl-A-COO-Phe-Hexyl
Alkyl-A-COO-Phe-Heptyl
Alkyl-A-COO-Phe-Octyl
Alkyl-A-COO-Phe-Nonyl
Alkyl-A-COO-Phe-Decyl
Alkyl-A-COO-Phe-Methoxy
Alkyl-A-COO-Phe-Ethoxy
Alkyl-A-COO-Phe-Propoxy
Alkyl-A-COO-Phe-Butoxy
Alkyl-A-COO-Phe-Pentoxy
Alkyl-A-COO-Phe-Hexoxy
Alkyl-A-COO-Phe-Heptoxy
Alkyl-A-COO-Phe-Octoxy
Alkyl-A-COO-Phe-Nonoxy
Alkyl-A-COO-Phe-Decoxy
Alkyl-A-COO-Cyc-CN
Alkyl-A-COO-Cyc-Methyl
Alkyl-A-COO-Cyc-Ethyl
Alkyl-A-COO-Cyc-Propyl
Alkyl-A-COO-Cyc-Butyl
Alkyl-A-COO-Cyc-Pentyl
Alkyl-A-COO-Cyc-Hexyl
Alkyl-A-COO-Cyc-Heptyl
Alkyl-A-COO-Cyc-Octyl
Alkyl-A-COO-Cyc-Nonyl
Alkyl-A-COO-Cyc-Decyl
Alkyl-A-COO-Phe-Phe-CN
Alkyl-A-COO-Phe-Phe-Methyl
Alkyl-A-COO-Phe-Phe-Ethyl
Alkyl-A-COO-Phe-Phe-Propyl
Alkyl-A-COO-Phe-Phe-Butyl
Alkyl-A-COO-Phe-Phe-Pentyl
Alkyl-A-COO-Phe-Phe-Hexyl
Alkyl-A-COO-Phe-Phe-Heptyl
Alkyl-A-COO-Phe-Phe-Octyl
Alkyl-A-COO-Phe-Phe-Nonyl
Alkyl-A-COO-Phe-Phe-Decyl
Alkyl-A-Phe-COO-Cyc-CN
Alkyl-A-Phe-COO-Cyc-Methyl
Alkyl-A-Phe-COO-Cyc-Ethyl
Alkyl-A-Phe-COO-Cyc-Propyl
Alkyl-A-Phe-COO-Cyc-Butyl
Alkyl-A-Phe-COO-Cyc-Pentyl
Alkyl-A-Phe-COO-Cyc-Hexyl
Alkyl-A-Phe-COO-Cyc-Heptyl
Alkyl-A-Phe-COO-Cyc-Octyl
Alkyl-A-Phe-COO-Cyc-Nonyl
Alkyl-A-Phe-COO-Cyc-Decyl
Alkyl-A-Phe-COO-Phe-CN
Alkyl-A-Phe-COO-Phe-Methyl
Alkyl-A-Phe-COO-Phe-Ethyl
Alkyl-A-Phe-COO-Phe-Propyl
Alkyl-A-Phe-COO-Phe-Butyl
Alkyl-A-Phe-COO-Phe-Pentyl
Alkyl-A-Phe-COO-Phe-Hexyl
Alkyl-A-Phe-COO-Phe-Heptyl
Alkyl-A-Phe-COO-Phe-Octyl
Alkyl-A-Phe-COO-Phe-Nonyl
Alkyl-A-Phe-COO-Phe-Decyl Alkyl-A-Phe-COO-Phe-Methoxy
Alkyl-A-Phe-COO-Phe-Ethoxy
Alkyl-A-Phe-COO-Phe-Propoxy
Alkyl-A-Phe-COO-Phe-Butoxy
Alkyl-A-Phe-COO-Phe-Pentoxy
Alkyl-A-Phe-COO-Phe-Hexoxy
Alkyl-A-Phe-COO-Phe-Heptoxy
Alkyl-A-Phe-COO-Phe-Octoxy
Alkyl-A-Phe-COO-Phe-Nonoxy
Alkyl-A-Phe-COO-Phe-Decoxy
Alkyl-A-Phe-COO-(3-F-Phe)-CN
Alkyl-A-Phe-CH$_2$CH$_2$-(3-F-Phe)-CN
Alkyl-A-Phe-CH$_2$O-(3-F-Phe)-CN
Alkyl-A-Cyc-COO-Cyc-CN
Alkyl-A-Cyc-COO-Cyc-Methyl
Alkyl-A-Cyc-COO-Cyc-Ethyl
Alkyl-A-Cyc-COO-Cyc-Propyl
Alkyl-A-Cyc-COO-Cyc-Butyl
Alkyl-A-Cyc-COO-Cyc-Pentyl
Alkyl-A-Cyc-COO-Cyc-Hexyl
Alkyl-A-Cyc-COO-Cyc-Heptyl
Alkyl-A-Cyc-COO-Cyc-Octyl
Alkyl-A-Cyc-COO-Cyc-Nonyl
Alkyl-A-Cyc-COO-Cyc-Decyl
Alkyl-A-Cyc-COO-Phe-CN
Alkyl-A-Cyc-COO-Phe-Methyl
Alkyl-A-Cyc-COO-Phe-Ethyl
Alkyl-A-Cyc-COO-Phe-Propyl
Alkyl-A-Cyc-COO-Phe-Butyl
Alkyl-A-Cyc-COO-Phe-Pentyl
Alkyl-A-Cyc-COO-Phe-Hexyl
Alkyl-A-Cyc-COO-Phe-Heptyl
Alkyl-A-Cyc-COO-Phe-Octyl
Alkyl-A-Cyc-COO-Phe-Nonyl
Alkyl-A-Cyc-COO-Phe-Decyl
Alkyl-A-Cyc-COO-Phe-Methoxy
Alkyl-A-Cyc-C00-Phe-Ethoxy
Alkyl-A-Cyc-COO-Phe-Propoxy
Alkyl-A-Cyc-COO-Phe-Butoxy
Alkyl-A-Cyc-COO-Phe-Pentoxy
Alkyl-A-Cyc-COO-Phe-Hexoxy
Alkyl-A-Cyc-COO-Phe-Heptoxy
Alkyl-A-Cyc-COO-Phe-Octoxy
Alkyl-A-Cyc-COO-Phe-Nonoxy or
Alkyl-A-Cyc-COO-Phe-Decoxy.

12. A phase according to claim 7 wherein said derivative is of the formula
Alkyl-A-OCO-Cyc-Methyl
Alkyl-A-OCO-Cyc-Ethyl
Alkyl-A-OCO-Cyc-Propyl
Alkyl-A-OCO-Cyc-Butyl
Alkyl-A-OCO-Cyc-Pentyl
Alkyl-A-OCO-Cyc-Hexyl
Alkyl-A-OCO-Cyc-Heptyl
Alkyl-A-OCO-Cyc-Octyl
Alkyl-A-OCO-Cyc-Nonyl
Alkyl-A-OCO-Cyc-Decyl
Alkyl-A-OCO-Phe-Methyl
Alkyl-A-OCO-Phe-Ethyl
Alkyl-A-OCO-Phe-Propyl
Alkyl-A-OCO-Phe-Butyl
Alkyl-A-OCO-Phe-Pentyl
Alkyl-A-OCO-Phe-Hexyl
Alkyl-A-OCO-Phe-Heptyl
Alkyl-A-OCO-Phe-Octyl
Alkyl-A-OCO-Phe-Nonyl
Alkyl-A-OCO-Phe-Decyl
Alkyl-A-OCO-Phe-Methoxy
Alkyl-A-OCO-Phe-Ethoxy
Alkyl-A-OCO-Phe-Propoxy
Alkyl-A-OCO-Phe-Butoxy
Alkyl-A-OCO-Phe-Pentoxy
Alkyl-A-OCO-Phe-Hexoxy
Alkyl-A-OCO-Phe-Heptoxy
Alkyl-A-OCO-Phe-Octoxy
Alkyl-A-OCO-Phe-Nonoxy
Alkyl-A-OCO-Phe-Decoxy
Alkyl-A-OCO-Dio-Methyl
Alkyl-A-OCO-Dio-Ethyl
Alkyl-A-OCO-Dio-Propyl
Alkyl-A-OCO-Dio-Butyl
Alkyl-A-OCO-Dio-Pentyl
Alkyl-A-OCO-Dio-Hexyl
Alkyl-A-OCO-Dio-Heptyl
Alkyl-A-OCO-Dio-Octyl
Alkyl-A-OCO-Dio-Nonyl or
Alkyl-A-OCO-Dio-Decyl.

13. A phase of claim 7 wherein said derivative is of the formula
Alkyl-A-CH$_2$CH$_2$-Phe-Phe-CN
Alkyl-A-CH$_2$CH$_2$-Phe-Phe-Methyl
Alkyl-A-CH$_2$CH$_2$-Phe-Phe-Ethyl
Alkyl-A-CH$_2$CH$_2$-Phe-Phe-Propyl
Alkyl-A-CH$_2$CH$_2$-Phe-Phe-Butyl
Alkyl-A-CH$_2$CH$_2$-Phe-Phe-Pentyl
Alkyl-A-CH$_2$CH$_2$-Phe-Phe-Hexyl
Alkyl-A-CH$_2$CH$_2$-Phe-Phe-Heptyl
Alkyl-A-CH$_2$CH$_2$-Phe-Phe-Octyl
Alkyl-A-CH$_2$CH$_2$-Phe-Phe-Nonyl
Alkyl-A-CH$_2$CH$_2$-Phe-Phe-Decyl
Alkyl-A-CH$_2$CH$_2$-Phe-(2-F-Phe)-CN
Alkyl-A-CH$_2$CH$_2$-Phe-(2-F-Phe)-Methyl
Alkyl-A-CH$_2$CH$_2$-Phe-(2-F-Phe)-Ethyl
Alkyl-A-CH$_2$CH$_2$-Phe-(2-F-Phe)-Propyl
Alkyl-A-CH$_2$CH$_2$-Phe-(2-F-Phe)-Butyl
Alkyl-A-CH$_2$CH$_2$-Phe-(2-F-Phe)-Pentyl
Alkyl-A-CH$_2$CH$_2$-Phe-(2-F-Phe)-Hexyl
Alkyl-A-CH$_2$CH$_2$-Phe-(2-F-Phe)-Heptyl
Alkyl-A-CH$_2$CH$_2$-Phe-(2-F-Phe)-Octyl
Alkyl-A-CH$_2$CH$_2$-Phe-(2-F-Phe)-Nonyl
Alkyl-A-CH$_2$CH$_2$-Phe-(2-F-Phe)-Decyl
Alkyl-A-CH$_2$CH$_2$-Phe-(2-F-Phe)-Methoxy
Alkyl-A-CH$_2$CH$_2$-Phe-(2-F-Phe)-Ethoxy
Alkyl-A-CH$_2$CH$_2$-Phe-(2-F-Phe)-Propoxy
Alkyl-A-CH$_2$CH$_2$-Phe-(2-F-Phe)-Butoxy
Alkyl-A-CH$_2$CH$_2$-Phe-(2-F-Phe)-Pentoxy
Alkyl-A-CH$_2$CH$_2$-Phe-(2-F-Phe)-Hexoxy
Alkyl-A-CH$_2$CH$_2$-Phe-(2-F-Phe)-Heptoxy
Alkyl-A-CH$_2$CH$_2$-Phe-(2-F-Phe)-Octoxy
Alkyl-A-CH$_2$CH$_2$-Phe-(2-F-Phe)-Nonoxy
Alkyl-A-CH$_2$CH$_2$-Phe-(2-F-Phe)-Decoxy
Alkyl-A-CH$_2$O-Phe-Pyr-Methyl
Alkyl-A-CH$_2$O-Phe-Pyr-Ethyl
Alkyl-A-CH$_2$O-Phe-Pyr-Propyl
Alkyl-A-CH$_2$O-Phe-Pyr-Butyl
Alkyl-A-CH$_2$O-Phe-Pyr-Pentyl
Alkyl-A-CH$_2$O-Phe-Pyr-Hexyl
Alkyl-A-CH$_2$O-Phe-Pyr-Heptyl
Alkyl-A-CH$_2$O-Phe-Pyr-Octyl
Alkyl-A-CH$_2$O-Phe-Pyr-Nonyl
Alkyl-A-CH$_2$O-Phe-Pyr-Decyl
Alkyl-A-CH$_2$CH$_2$-Cyc-CN
Alkyl-A-CH$_2$CH$_2$-Cyc-Methyl
Alkyl-A-CH$_2$CH$_2$-Cyc-Ethyl Alkyl-A-CH2CH2-Cyc-Propyl
Alkyl-A-CH2CH2-Cyc-Butyl
Alkyl-A-CH2CH2-Cyc-Pentyl
Alkyl-A-CH2CH2-Cyc-Hexyl
Alkyl-A-CH2CH2-Cyc-Heptyl
Alkyl-A-CH2CH2-Cyc-Octyl
Alkyl-A-CH2CH2-Cyc-Nonyl or
Alkyl-A-CH2CH2-Cyc-Decyl.

14. In a liquid-crystal display element comprising a liquid-crystalline phase, the improvement wherein the phase is one of claim 1.

15. In an electrooptical display element comprising a liquid-crystalline dielectric, the improvement wherein the dielectric is a phase of claim 1.

16. A phase of claim 1 wherein said derivative is of the formula $R^1—A^1—Z^1—A^2—R^2$ wherein
each of $R^1$ and $R^2$ independently is alkyl of 1-15 C atoms, or alkyl of 1-15 C atoms in which one or two nonadjacent CH2 groups are replaced by —O—, —O—CO—, or —CO—O— and one of $R^1$ and $R^2$ can also be H, F, Cl, Br, CN, or $R^3—A^3—Z^2$,
$A^1$ is —A—, —$A^4$—A—, or —A—$A^4$—,
A is

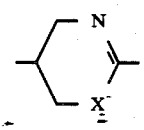

X is O or S,
each of $A^2$, $A^3$ and $A^4$ independently is a 1.4-cyclohexylene, 1,3-dioxane-2,5-diyl or a 1,3-dithiane-2,5-diyl group; is a piperidine-1,4-diyl, 1,4-bicyclo-[2.2.2]-octylene, A or 1,4-phenylene group; or is a 1,4-phenylene group in which one or two CH groups may also be replaced by N;
each of $Z^1$ and $Z^2$ independently is —CO—O—, —O—CO—, —CH2CH2—, —CHCN—CH2—, —CH2—CHCN—, —OCH2—, —CH2O—, or a single bond and
$R^3$ is alkyl of 1-15 C atoms, alkyl of 1-15 C atoms in which one or two nonadjacent CH2 groups are replaced by —O—, —CO—, —O—CO—, or —CO—O— or H, F, Cl, Br, or CN.

17. A phase of claim 1 wherein said derivative is of the formula $R^1—A—A^2A^3—R^3$ wherein
$R^1$ is alkyl of 1-15 C atoms,
A is

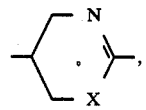

X is O or S,
$A^2$ is CY or Phe,
$A^3$ is missing or is Cy or Phe and
$R^3$ is alkyl of 1-15 C atoms, or alkyl of 1-15 C atoms in which one or two nonadjacent CH2 groups are replaced by —O—, or F, CL, Br, or CN.

18. A phase of claim 1 wherein said derivative is of the formula $R^1—A—A^2—A^3—R^3$ wherein
$R^1$ is alkyl of 1-15 C atoms,
A is

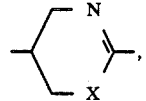

X is O or S,
$A^2$ is Cy or Phe,
$A^3$ is missing or is Cy or Phe and
$R^3$ is alkyl or alkoxy of 1-15 C atoms, F, CL, Br, or CN.

* * * * *